United States Patent
Sjogren et al.

(10) Patent No.: US 10,851,118 B2
(45) Date of Patent: *Dec. 1, 2020

(54) COMPOSITIONS AND METHODS FOR INHIBITING ARGINASE ACTIVITY

(71) Applicant: CALITHERA BIOSCIENCES, INC., South San Francisco, CA (US)

(72) Inventors: Eric B. Sjogren, Mountain View, CA (US); Jim Li, San Francisco, CA (US); Michael Van Zandt, Guilford, CT (US); Darren Whitehouse, Westbrook, CT (US)

(73) Assignee: CALITHERA BIOSCIENCES, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/101,275

(22) Filed: Aug. 10, 2018

(65) Prior Publication Data

US 2018/0346489 A1 Dec. 6, 2018

Related U.S. Application Data

(62) Division of application No. 15/337,041, filed on Oct. 28, 2016, now Pat. No. 10,065,974.

(60) Provisional application No. 62/323,034, filed on Apr. 15, 2016, provisional application No. 62/281,964, filed on Jan. 22, 2016, provisional application No. 62/248,632, filed on Oct. 30, 2015.

(51) Int. Cl.

| | | |
|---|---|---|
| *C07F 5/02* | (2006.01) | |
| *C07K 16/28* | (2006.01) | |
| *A61K 31/69* | (2006.01) | |
| *A61K 39/395* | (2006.01) | |
| *A61K 45/06* | (2006.01) | |
| *A61K 39/00* | (2006.01) | |

(52) U.S. Cl.
CPC ............. *C07F 5/025* (2013.01); *A61K 31/69* (2013.01); *A61K 39/3955* (2013.01); *A61K 39/39533* (2013.01); *A61K 45/06* (2013.01); *C07K 16/2818* (2013.01); *A61K 2039/507* (2013.01)

(58) Field of Classification Search
CPC ... C07F 5/025; A61K 31/69; A61K 39/39533; A61K 39/3955; A61K 45/06; A61K 2039/507; C07K 16/2818
See application file for complete search history.

(56) References Cited

U.S. PATENT DOCUMENTS

| | | |
|---|---|---|
| 8,894,970 B2 | 11/2014 | Tomczuk et al. |
| 9,200,011 B2 | 12/2015 | Van Zandt et al. |
| 9,233,985 B2 | 1/2016 | Van Zandt et al. |
| 9,266,908 B2 | 2/2016 | Van Zandt et al. |
| 9,440,995 B2 | 9/2016 | Van Zandt et al. |
| 2002/0081626 A1 | 6/2002 | Kaddurah-Daouk et al. |
| 2004/0063666 A1 | 1/2004 | Christianson et al. |
| 2010/0189644 A1 | 7/2010 | Christianson et al. |
| 2012/0083469 A1 | 4/2012 | Van Zandt et al. |
| 2012/0129806 A1* | 5/2012 | Van Zandt ............... A61P 11/00 514/64 |
| 2014/0371175 A1 | 12/2014 | Van Zandt et al. |
| 2015/0080341 A1 | 3/2015 | Van Zandt et al. |
| 2015/0191492 A1 | 7/2015 | Van Zandt et al. |
| 2016/0375044 A1 | 12/2016 | Gross et al. |

FOREIGN PATENT DOCUMENTS

| | | |
|---|---|---|
| CA | 2431080 A1 | 12/2004 |
| CN | 103068830 A | 4/2013 |
| CN | 103402549 A | 11/2013 |
| CN | 105879030 A | 8/2016 |
| WO | WO-1999019295 A1 | 4/1999 |
| WO | WO-2007005620 A2 | 1/2007 |
| WO | WO-2010085797 A2 | 7/2010 |
| WO | WO-2011133653 A1 | 10/2011 |
| WO | WO-2012058065 A1 | 5/2012 |
| WO | WO-2012091757 A1 | 7/2012 |
| WO | WO-2013059437 A1 | 4/2013 |
| WO | WO-2013059587 A1 | 4/2013 |
| WO | WO-2013158262 A1 | 10/2013 |
| WO | WO-2015061752 A1 | 4/2015 |
| WO | WO-2016153078 A1 | 9/2016 |
| WO | WO-2016210106 A1 | 12/2016 |

OTHER PUBLICATIONS

Ajinomoto Amino Acids Link News Aug. 2005 vol. 11: 3-4.
Arina, A. et al. 2014 "Adoptively Transferred Immune T Cells Eradicate Established Tumors despite Cancer-Induced Immune Suppression," *J Immunol* 192: 1286-1293.
Baggio et al. 1997 "Inhibition of Mn2+ 2-Arginase by Borate Leads to the Design of a Transition State Analogue Inhibitor, 2(S)-Amino-6-boronohexanoic Acid," *J Am Chem Soc* 119(34): 8107-8108.
Barbul, A. 1990 "Arginine and Immune Function," Nutrition 6(1) 53-58.
Bartolucci et al. 2012 "Direct, Regioselective and Chemoselective Preparation of Novel Boronated Tryptophans by Friedel-Crafts Alkylation" *Organic Letters* 14(2): 600-603.
Busnel et al. 2005 "Synthesis and evaluation of new co-borono-a-amino acids as rat liver arginase inhibitors," *Bioorg Med Chem* 13(7): 2373-2379.
Calithera Biosciences, Inc. Poster, SITC Conference; Nov. 9-13, 2016; National Harbor, MD.
Calithera Biosciences, Inc. Poster, EORTC-NCI-AACR; Nov. 29-Dec. 2, 2016; Munich, Germany.

(Continued)

*Primary Examiner* — Jeffrey S Lundgren
*Assistant Examiner* — Ibrahim D Bori
(74) *Attorney, Agent, or Firm* — Carl A. Morales; Seth E. Snyder; Dechert LLP

(57) ABSTRACT

The invention relates to a novel class of compounds that exhibit activity inhibitory activity toward arginase, and pharmaceutical compositions comprising the compounds of the invention. Also provided herein are methods of treating cancer with the arginase inhibitors of the invention.

38 Claims, 5 Drawing Sheets

(56) References Cited

OTHER PUBLICATIONS

CAS Registry No. 1374395-07-9. CA Index Name: "3-Pyrrolidinecarboxylic acid, 3-amino-4-(3-boronopropyl)-14(5,7-dichloro-1,2,3,4-tetrahydro-3-isoquinolinyl)carbonyll-, (3R,4S)-rel-". STN Entry Date: May 24, 2012 (Last update: May 28, 2012).
Colleluori et al. 2001 "Classical and Slow-Binding Inhibitors of Human Type II . Arginase", *Biochem*, 40(31): 9356-9362.
Curtis, B. et al. 2013 "Secondary amines containing one aromatic nitro group: preparation, nitrosation, sustained nitric oxide release, and the synergistic effects of released nitric oxide and an arginase inhibitor on vascular smooth muscle cell proliferation," *Bioorganic & medicinal chemistry* 21(5) 1123-1135. Retrieved from: <https://www.ncbi.nlm.nih.gov/pmc/articles/PMC3574223/pdf/nihms434525.pdf>.
Ellyard et al. 2010 "Alternatively Activated Macrophage Possess Antitumor Cytotoxicity That Is Induced by IL-4 and Mediated by Arginase-1," *J Immunother* 33: 443-452.
Geiger, Roger et al. 2016 "L-Arginine Modulates T Cell Metabolism and Enhances Survival and Anti-tumor Activity," *Cell, Cell Press* 167(3): 829ff.
Gritli-Linde, A. et al. 1998 "Opposing effects of suramin and DL-alpha-difluoromethylornithine on polyamine metabolism contribute to a synergistic action on B16 melanoma cell growth in vitro," *Anticancer Research* 18(2A) 863-870.
Hörig et al. 2004 "From bench to clinic and back: Perspective on the 1st IQPC Translational Research conference," *J Translational Med*, 2:44 doi:10.1186/1479-5876-2-44.
Ilies et al. 2011 "Binding of alpha,alpha-Disubstituted Amino Acids to Arginase Suggests New Avenues for Inhibitor Design," *J Med Chem* 54(15): 5432-5443.
International Preliminary Report on Patentability for International Application No. PCT/US2011/033223 dated Oct. 23, 2012. [CBH-012.25].
International Preliminary Report on Patentability for International Application No. PCT/US2013/030930 dated Oct. 30, 2014. [CBH-014.25].
International Search Report and Written Opinion for International Application No. PCT/US2011/033223 dated Jul. 14, 2011. [CBH-012.25].
International Search Report and Written Opinion for International Application No. PCT/US2011/056844 dated Dec. 14, 2011. [CBH-013.25].
International Search Report and Written Opinion for International Application No. PCT/US2012/060789 dated Dec. 19, 2012. [CBH-011.25].
International Search Report and Written Opinion for International Application No. PCT/US2013/030930 dated May 23, 2013. [CBH-014.25].
International Search Report and Written Opinion for International Application No. PCT/US2016/038983 dated Dec. 29, 2016 [026WO].
International Preliminary Report on Patentability for International Application No. PCT/US2016/038983 dated Dec. 26, 2017 [026WO].
International Preliminary Report on Patentability for International Application No. PCT/US2016/059342 dated May 11, 2018 [028WO].
Ivanenkov et al.2014 "Small-molecule arginase inhibitors," *Pharm Pat Anal* 3(1): 65-85.
Kabalka et al. 2008 "Synthesis of a series of boronated unnatural cyclic amino acids as potential boron neutron capture therapy agents," *Appl Organomet Chem*, 22(9): 516-522.
Koziara et al. 2004 "Paclitaxel nanooparticles for the potential treatment of brain tumors," *J Controlled Release* 99: 259-269.
Lei et al. 2009 "Progress of Boronic Acids as Enzyme Inhibitors" *Chinese J Pharm* 40(3): 213-219 (English Abstract only).

Li, L. et al. "An Engineered Arginase FC Protein Inhibits Tumor Growth In Vitro and In Vivo," *Evidence-Based Complementary and Alternative Medicine* vol. 2013, Article ID 243129: 1-9.
Lorvik, Kristina Berg et al. 2016 "Adoptive Transfer of Tumor-Specific Th2Cells Eradicates Tumors by Triggering an in Situ Inflammatory Immune Response," *Cancer Research* 76(23): 6864-6876.
Raber, P. et al. 2012 Metabolism of L-Arginine by Myeloid-Derived Suppressor Cells in Cancer: Mechanisms of T cell suppression and Therapeutic Perspectives *Immunol Invest* 41(6-7): 614-634.
Raber, P. et al. 2016 "T cells conditioned with MDSC show an increased anti-tumor activity after adoptive T cell base immunotherapy," *Oncotarget* 7(14): 17565-17578.
Rodriguez, P. et al. 2003 "L-Arginine Consumption by Macrophages Modulates the Expression of CD3$\chi$ Chain in T Lymphocytes," *J Immunol* 17: 1232-1239.
Rodriguez, P. et al. 2004 "Arginase I Production in the Tumor Microenvironment by Mature Myeloid Cells Inhibits T-Cell Receptor Expression and Antigen-Specific T-Cell Responses," *Cancer Research* 64: 5839-5849.
Rodriguez, P. et al. 2008 "Arginine regulation by myeloid derived suppressor cells and tolerance in cancer: mechanisms and therapeutic perspectives," *Immunol Rev* 222: 180-191.
Rossnagl, Stephanie et al. 2016, "EDA-Fibronectin Originating from Osteoblasts Inhibits the Immune Response against Cancer," *PLOS Biology* 14(9): e1002562.
Sandgren, S. and Belting, M. 2003 "Suramin Selectively inhibits carcinoma cell growth that is dependent on extracellular polyamines," *Anticancer Research* 23(2B): 1223-1228.
Schafer, et al. 2008 "Failure is an option: learning from unsuccessful proof-of-concept trials," *Drug Discov Today*, 13(21): 913-916.
Scheit, K. and Bauer, G. 2014 "Synergistic effects between catalase inhibitors and modulators of nitric oxide metabolism on tumor cell apoptosis," *Anticancer Research* 34(10): 5337-5350. Retrieved from: <https://ar.iiarj ournals.org/content/34/10/5337.full.pdf+html>.
Segal et al. 2012 "Chronic Oral Administration of the Arginase Inhibitors 2(S)-amino-6-boronohexanoic Acid (ABH) Improves Erectile Function in Aged Rates," *J Androl*, 33(6): 11691175.
Selamnia, M. et al. 1998 "$\alpha$-Difluoromethylornithine (DFMO) as a potent arginase activity inhibitor in human colon carcinoma cells," *Biochemical pharmacology* 55(8): 1241-1245.
Singh, S. et al. 2000 "Arginase Activity in Human Breast Cancer Cell Lines: $N^\omega$-Hydroxy-L-arginine Selectively Inhibits Cell Proliferation and Induces Apoptosis in MDA-MB-468 Cells" *Cancer Research* 60: 3305-3312.
Steggerda, Susanne M. et al. 2016 "Abstract B045: Arginase inhibitor CB-1158 elicits immune-mediated antitumor responses as a single agent and in combination with other immunotherapies," Second CRI-CIMT-EATI-AACR International Cancer Immunotherapy Conference: Translating Science into Survival; Sep. 25-28, 2016; New York, NY.
Steggerda, Susanne M. et al. 2017, "Inhibition of arginase by CB-1158 blocks myeloid cell-mediated immune suppression in the tumor microenvironment," *Journal for ImmunoTherapy of Cancer* 5(1): 1-18.
Steppan et al. 2013 "Development of novel arginase inhibitors for therapy of endothelial dysfunction," *Front Immunol* 51(4): 5905-5908.
Tate et al. 2008 "Effect of arginase II on L-arginine depletion and cell growth in murine cell lines of renal cell carcinoma," *J Hematol Oncol* 1(14): 1-10.
Vissers, Y. et al. 2005 "Plasma arginine concentrations are reduced in cancer patients: evidence for arginine deficiency?" *Am J Chn Nutr* 81: 1142-1146.

\* cited by examiner

A

B

COMPOSITIONS AND METHODS FOR INHIBITING ARGINASE ACTIVITY

RELATED APPLICATIONS

This application is a divisional of U.S. application Ser. No. 15/337,041, filed on Oct. 28, 2016, now U.S. Pat. No. 10,065,974, which claims the benefit of priority to U.S. Provisional Patent Application No. 62/248,632, filed Oct. 30, 2015; U.S. Provisional Patent Application No. 62/281,964, filed Jan. 22, 2016; and U.S. Provisional Patent Application No. 62/323,034, filed Apr. 15, 2016, which applications are hereby incorporated by reference in their entirety.

BACKGROUND

Cancer is characterized by the uncontrolled growth of cells in the body, leading to the invasion of essential organs and often death. Initially, the pharmacological treatment of cancer utilized non-specific cytotoxic agents that targeted all rapidly dividing cells, including normal cells. These non-specific cytotoxic agents have anti-tumor effects but their use is often limited by severe toxicities. As the understanding of the proteins and pathways that enable cancer cells to thrive has evolved, newer more targeted agents have been developed that block specific proteins that are activated in cancer cells.

An emerging field for the development of therapeutics that addresses the challenges presented in treating cancers is immuno-oncology, also referred to as tumor immunology. Certain tumor types have developed mechanisms to escape destruction by the body's immune system. Tumor immunology is a therapeutic area focused on activating the body's own immune system to attack and kill tumors. The naturally occurring amino acid arginine is implicated in tumor immunology, as it is important for the activation, growth, and survival of a body's cancer-fighting cytotoxic T-cells. However, levels of arginine are depleted in the tumor microenvironment by arginase, an enzyme produced and secreted by neutrophils and myeloid derived suppressor cells (MDSCs) that accumulate in cancer patients of multiple histotypes. In fact, elevated levels of arginase enzyme have been observed in the plasma of renal cell carcinoma, breast cancer, chronic myelogenous leukemia, esophageal cancer, prostate cancer, non-small cell lung cancer, glioblastoma, and acute myeloid leukemia patients. Therefore, there is a need to develop inhibitors of arginase that restore arginine levels in the tumor microenvironment, therefore promoting the tumor-killing activity of cytotoxic T-cells.

SUMMARY OF INVENTION

In certain embodiments, the invention provides a series of novel arginase inhibitor compounds. The compounds of the invention have a structure of formula (I):

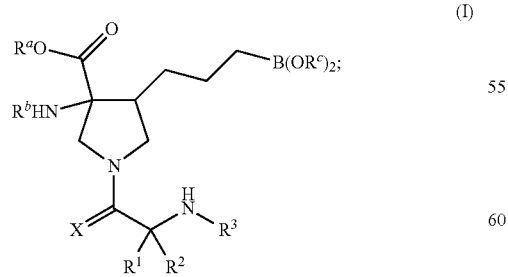

(I)

or a pharmaceutically acceptable salt or prodrug thereof; wherein:

$R^a$ is H or is selected from optionally substituted alkyl, alkenyl, alkynyl, cycloalkyl, heterocycloalkyl, (cycloalkyl)alkyl, (heterocycloalkyl)alkyl, aryl, heteroaryl, aralkyl, and heteroaralkyl;

$R^b$ is H or is selected from optionally substituted alkyl, alkenyl, alkynyl, acyl, —C(O)O(alkyl), and —C(O)O(aryl);

each $R^c$ is independently selected from H or alkyl, or two occurrences of $R^c$ are taken together with the intervening —O—B—O— atoms to form an optionally substituted boron-containing ring;

X is O or S;

$R^1$ and $R^2$ are each independently selected from H and optionally substituted alkyl, alkenyl, alkynyl, cycloalkyl, (cycloalkyl)alkyl, heterocycloalkyl, (heterocycloalkyl)alkyl, aryl, heteroaryl, aralkyl, and heteroaralkyl;

or $R^1$ and $R^2$ are taken together with the intervening atoms to form an optionally substituted 5- to 7-membered ring; and $R^3$ is H or optionally substituted alkyl;

or $R^1$ and $R^3$ are taken together with the intervening atoms to form an optionally substituted 5- to 7-membered ring;

wherein the compound is not:

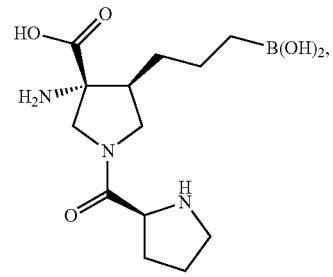

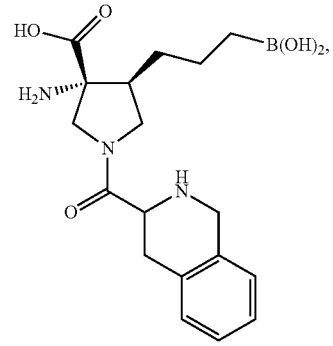

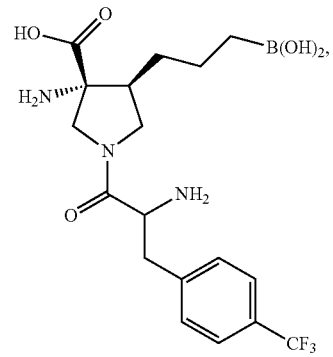

-continued

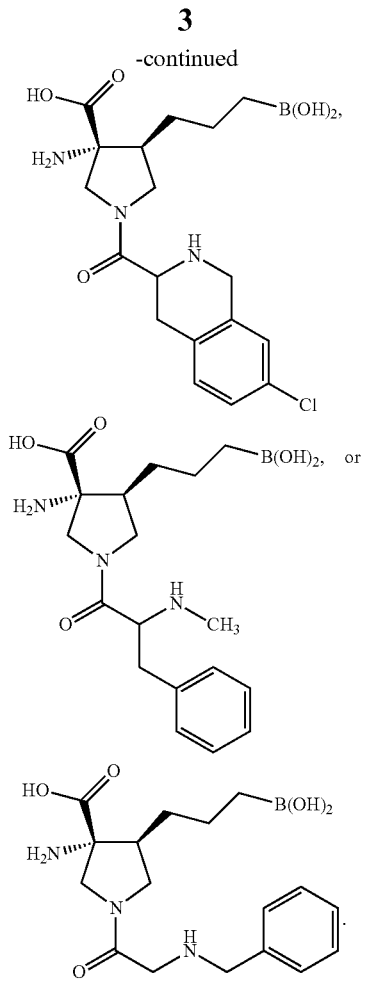

In certain embodiments, the invention also provides pharmaceutical compositions comprising a compound of the invention and a pharmaceutically acceptable carrier.

In certain embodiments, the invention provides methods of treating or preventing cancer, comprising administering to a subject in need thereof a therapeutically effective amount of a compound or pharmaceutical composition of the invention.

DETAILED DESCRIPTION OF THE INVENTION

Figure 1:
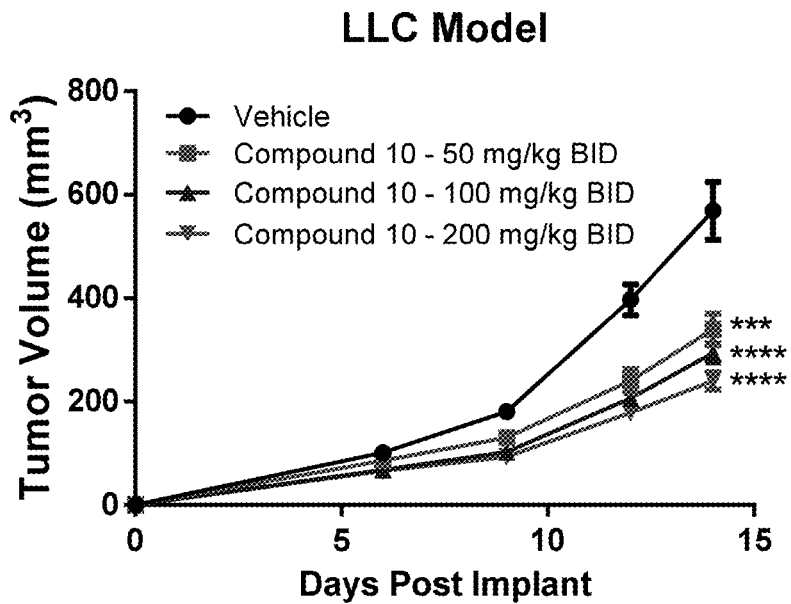
FIG. 1 is a graph depicting the tumor volume over time. Arginase inhibitor Compound 10, administered as a single agent, slows tumor growth relative to control in mice implanted with Lewis Lung Carcinoma cells.

The present invention provides small molecule inhibitors of arginase.

Compounds of the Invention

In certain embodiments, the invention provides a compound having a structure of formula (I):

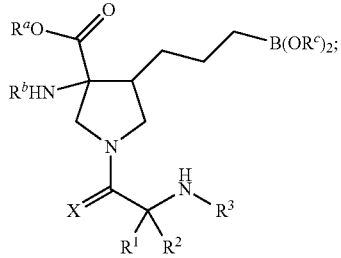

(I)

or a pharmaceutically acceptable salt or prodrug thereof; wherein:

$R^a$ is H or is selected from optionally substituted alkyl, alkenyl, alkynyl, cycloalkyl, heterocycloalkyl, (cycloalkyl)alkyl, (heterocycloalkyl)alkyl, aryl, heteroaryl, aralkyl, and heteroaralkyl;

$R^b$ is H or is selected from optionally substituted alkyl, alkenyl, alkynyl, acyl, —C(O)O(alkyl), and —C(O)O (aryl);

each $R^c$ is independently selected from H or alkyl, or two occurrences of $R^c$ are taken together with the intervening —O—B—O— atoms to form an optionally substituted boron-containing ring;

X is O or S;

$R^1$ and $R^2$ are each independently selected from H and optionally substituted alkyl, alkenyl, alkynyl, cycloalkyl, (cycloalkyl)alkyl, heterocycloalkyl, (heterocycloalkyl)alkyl, aryl, heteroaryl, aralkyl, and heteroaralkyl; or $R^1$ and $R^2$ are taken together with the intervening atoms to form an optionally substituted 5- to 7-membered ring; and $R^3$ is H or optionally substituted alkyl;

or $R^1$ and $R^3$ are taken together with the intervening atoms to form an optionally substituted 5- to 7-membered ring;

wherein the compound is not:

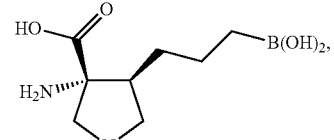

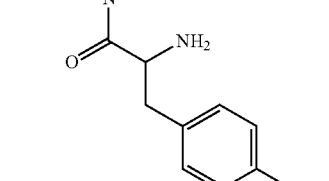

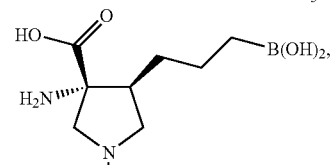

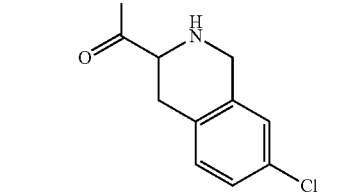

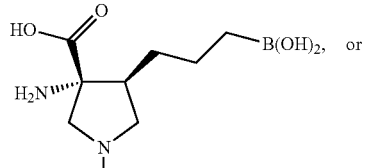

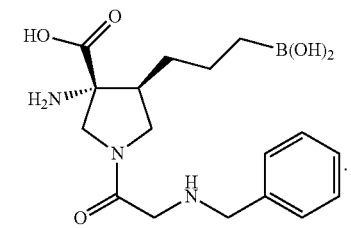 [SMILES: N[C@@]1(C(=O)O)CN(C(=O)CNCc2ccccc2)C[C@@H]1CCCB(O)O]

In certain embodiments, the compound of formula (I) has a structure of formula (Ia):

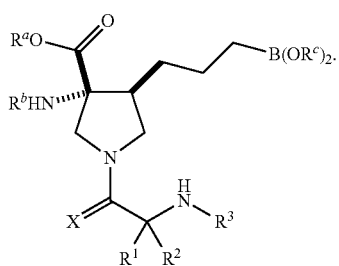

(Ia)

In certain embodiments, the compound of formula (I) has a structure of formula (Ib):

(Ib)

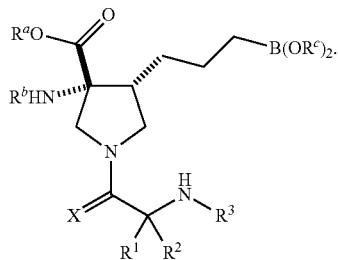

In certain embodiments, the compound of formula (I) has a structure of formula (Ic):

(Ic)

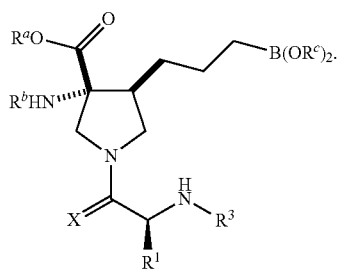

In certain embodiments, the compound of formula (I) has a structure of formula (Id):

(Id)

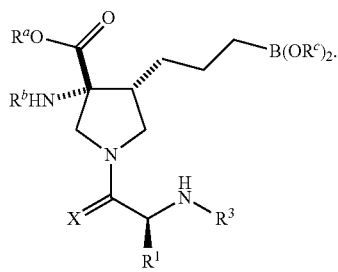

In certain embodiments, the compound of formula (I) has a structure of formula (Ie):

(Ie)

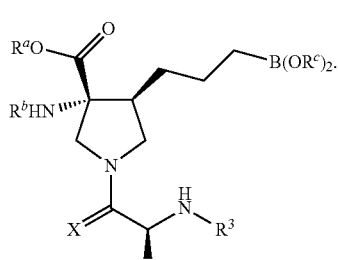

In certain embodiments, the compound of formula (I) has a structure of formula (If):

(If)

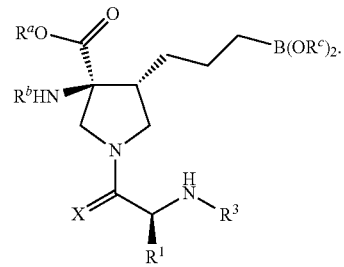

In certain embodiments, the compound of formula (I) has a structure of formula (Ig):

(Ig)

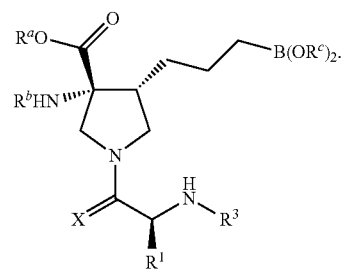

In certain embodiments, the compound of formula (I) has a structure of formula (Ih):

(Ih)

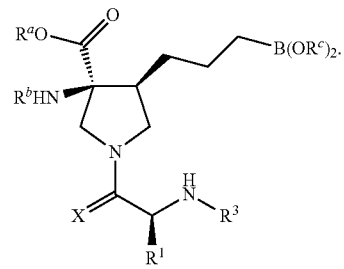

In certain embodiments of any of formulae (I), (Ia), and (Ib), $R^2$ is H.

In certain embodiments of any of the foregoing formulae, $R^a$ is H or optionally substituted alkyl. In certain preferred embodiments, $R^a$ is H.

In certain embodiments of any of the foregoing formulae, $R^b$ is H or optionally substituted alkyl or acyl. In certain preferred embodiments, $R^b$ is H.

In certain embodiments of any of the foregoing formulae, $R^c$ is H for each occurrence.

In certain embodiments of any of the foregoing formulae, two occurrences of $R^c$ are taken together to form an optionally substituted dioxaborolane, dioxaborolanone, dioxaborolandione, dioxaborinane, dioxaborinanone, or dioxaborinandione.

In certain embodiments of any of the foregoing formulae, X is O.

In certain embodiments of any of the foregoing formulae, if $R^1$ is H, then $R^3$ is not benzyl.

In certain embodiments of any of the foregoing formulae, $R^1$ is H.

In certain embodiments of any of the foregoing formulae, if R¹ is benzyl, then R³ is not methyl.

In certain embodiments, R¹ is optionally substituted aralkyl, heteroaralkyl, (cycloalkyl)alkyl, or (heterocycloalkyl)alkyl.

In certain embodiments, R¹ is optionally substituted aralkyl or heteroaralkyl.

In certain such embodiments, R¹ is benzyl.

In other certain such embodiments, R¹ is not benzyl substituted by —CF₃.

In yet other certain such embodiments, R¹ is heteroaralkyl, such as —CH₂-(1H-imidazol-4-yl).

In certain embodiments of any of the foregoing formulae R¹ is optionally substituted alkyl, alkenyl, or alkynyl.

In certain such embodiments, R¹ is alkyl, optionally substituted by one or more substituents independently selected from hydroxy, halo, haloalkyl, alkoxy, —SH, —S-(alkyl), —SeH, —Se-(alkyl), aryl, heteroaryl, cycloalkyl, heterocycloalkyl, amino, carboxylic acid, ester, guanidino, and amido.

In certain such embodiments, R¹ is alkyl, optionally substituted by one or more substituents independently selected from hydroxy, halo, haloalkyl, alkoxy, —SH, —S-(alkyl), —SeH, —Se-(alkyl), heteroaryl, cycloalkyl, heterocycloalkyl, amino, carboxylic acid, ester, guanidino, and amido.

In certain such embodiments, R¹ is alkyl, optionally substituted by one or more substituents independently selected from hydroxy, alkoxy, haloalkyl, and —S-(alkyl).

In certain embodiments, R¹ is selected from optionally substituted cycloalkyl, heterocycloalkyl, aryl, and heteroaryl.

In certain embodiments, R¹ is an amino acid side chain of Arg, His, Lys, Asp, Glu, Ser, Thr, Asn, Gln, Cys, Sec, Gly, Ala, Val, Ile, Leu, Met, Phe, Tyr, or Trp.

In certain embodiments, R¹ and R² are taken together with the intervening atoms to form an optionally substituted 5- to 7-membered ring.

In certain embodiments, R¹ and R² are taken together with the intervening atoms to form an optionally substituted 3- to 7-membered ring, such as a 3-membered ring.

In certain embodiments, R³ is H.

In certain embodiments, R¹ and R³ are taken together with the intervening atoms to form a substituted 5-membered ring.

In certain embodiments, R¹ and R³ are taken together with the intervening atoms to form an optionally substituted 6- or 7-membered ring.

In certain embodiments, R¹ and R³, taken together with the intervening atoms, do not form a tetrahydroisoquinolinyl ring, e.g.,

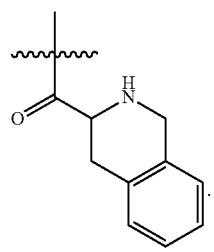 [SMILES: *C(=O)C1Cc2ccccc2CN1]

In certain embodiments, the compound of formula (I) is not:

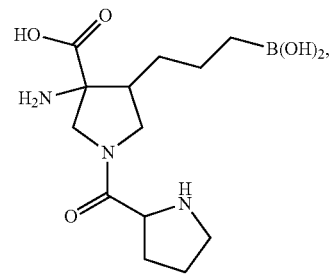

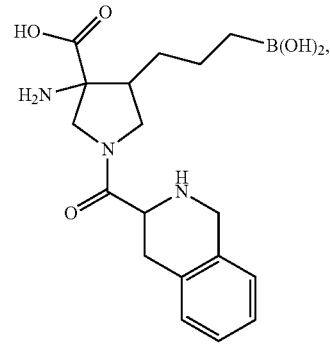

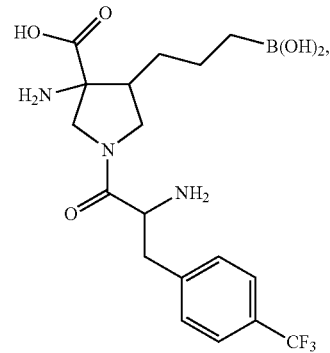

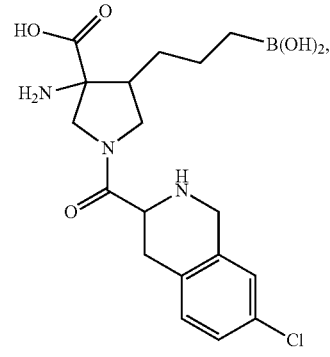

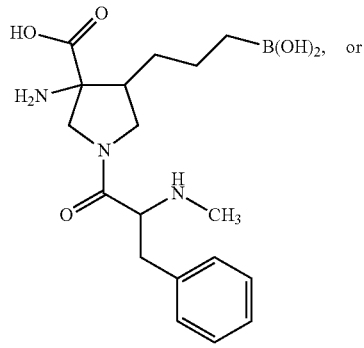

-continued
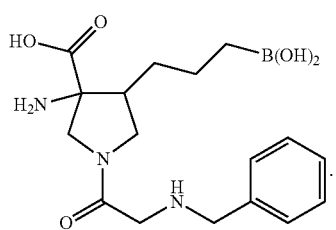 [SMILES: NC1(C(=O)O)CN(C(=O)CNCc2ccccc2)CC1CCCB(O)O]
In certain embodiments, the compound of the invention has a structure selected from:
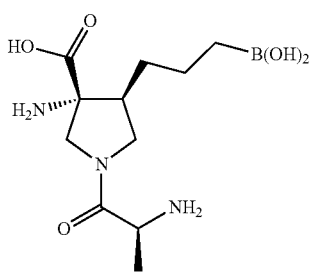
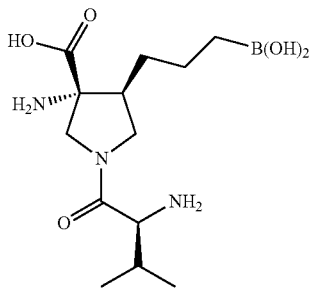
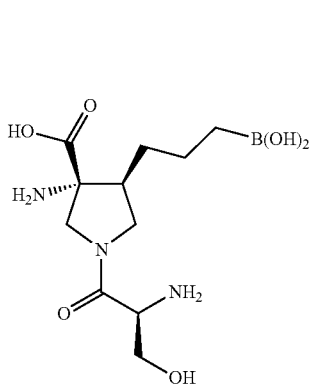
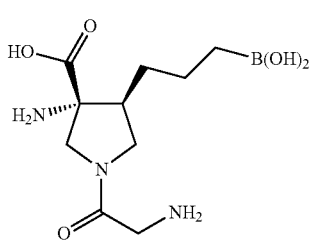
-continued
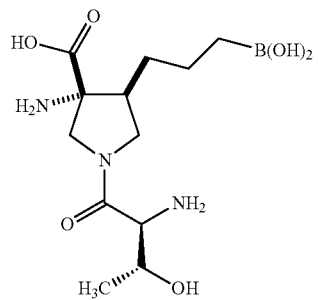
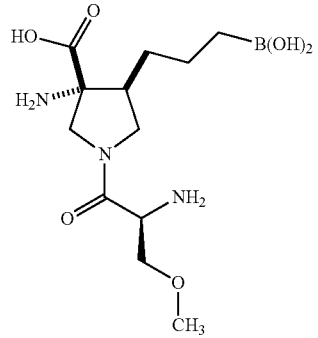
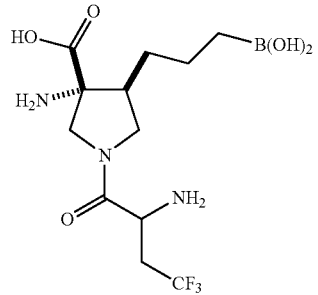
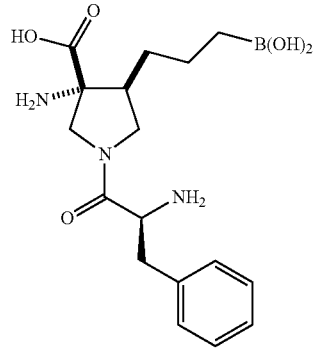
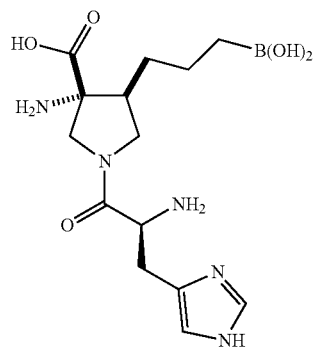

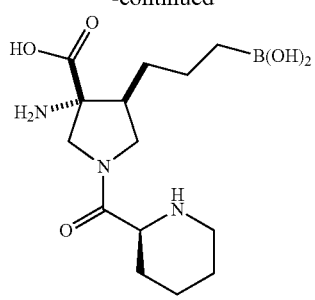
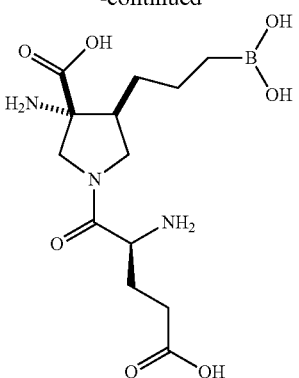
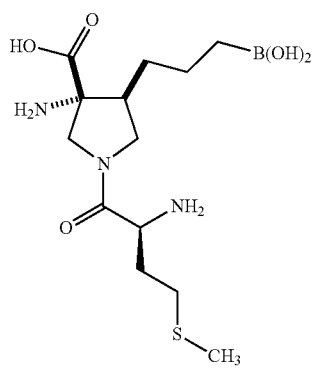
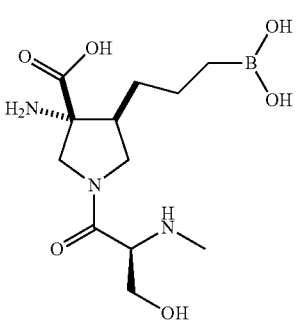
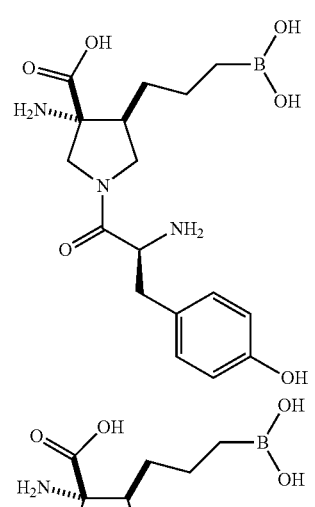
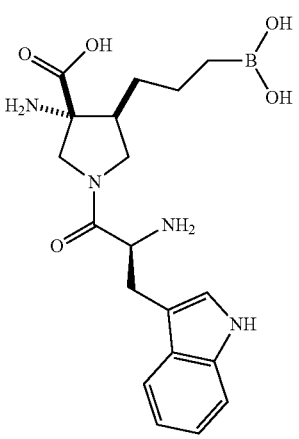
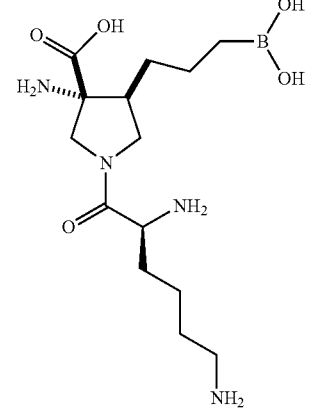
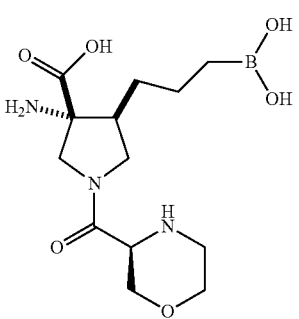

-continued

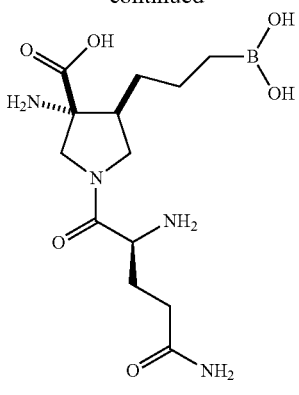

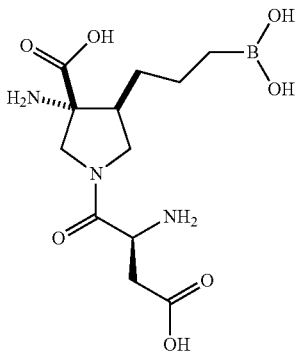

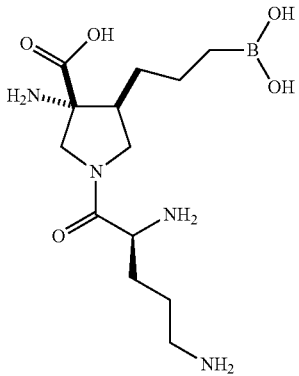

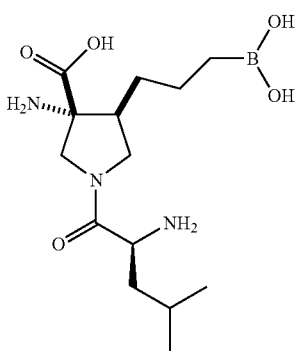

-continued

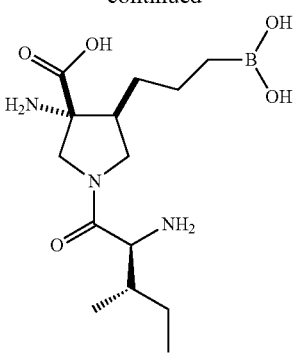

or a pharmaceutically acceptable salt or prodrug thereof.

In certain embodiments, the compound may be a prodrug, e.g., wherein a hydroxyl in the parent compound is presented as an ester or a carbonate, a carboxylic acid present in the parent compound is presented as an ester, or an amino group is presented as an amide. In certain such embodiments, the prodrug is metabolized to the active parent compound in vivo (e.g., the ester is hydrolyzed to the corresponding hydroxyl or carboxylic acid).

In certain embodiments, the boronic acid may exist in the form of a cyclic or linear anhydride. In certain embodiments, the boronic acid exists in the form of a 6-membered ring anhydride, and is also known as a boroxine.

In certain embodiments, arginase inhibitor compounds of the invention may be racemic. In certain embodiments, arginase inhibitor compounds of the invention may be enriched in one enantiomer. For example, a compound of the invention may have greater than 30% ee, 40% ee, 50% ee, 60% ee, 70% ee, 80% ee, 90% ee, or even 95% or greater ee.

The compounds of the invention have more than one stereocenter. Accordingly, the compounds of the invention may be enriched in one or more diastereomers. For example, a compound of the invention may have greater than 30% de, 40% de, 50% de, 60% de, 70% de, 80% de, 90% de, or even 95% or greater de. In certain embodiments, the compounds of the invention have substantially one isomeric configuration at one or more stereogenic centers, and have multiple isomeric configurations at the remaining stereogenic centers.

In certain embodiments, the enantiomeric excess of the stereocenter bearing $R^1$ is at least 40% ee, 50% ee, 60% ee, 70% ee, 80% ee, 90% ee, 92% ee, 94% ee, 95% ee, 96% ee, 98% ee or greater ee.

As used herein, single bonds drawn without stereochemistry do not indicate the stereochemistry of the compound. The compound of formula (I) provides an example of a compound for which no stereochemistry is indicated.

As used herein, hashed or bolded non-wedge bonds indicate relative, but not absolute, stereochemical configuration (e.g., do not distinguish between enantiomers of a given diastereomer). For example, in formula (Ia),

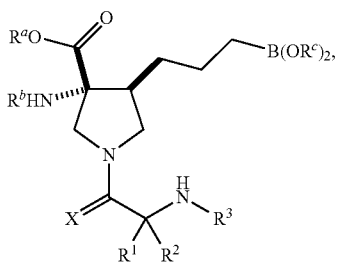

(Ia)

the bold, non-wedge bonds indicate that the —CO₂Rᵃ group and the (CH₂)₃B(ORᶜ)₂ group are configured to be cis to one another, but the bold, non-wedge bonds do not represent the absolute (i.e., R or S) configuration of the compound.

As used herein, hashed or bolded wedge bonds indicate absolute stereochemical configuration. For example, in formula (Ic).

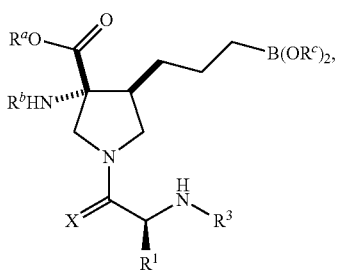

(Ic)

the bold, wedge bond indicates the absolute configuration of the stereocenter to which it is attached, while the bold, non-wedge bonds indicate that the —CO₂Rᵃ group and the (CH₂)₃B(ORᶜ)₂ group are configured to be cis to one another, but do not indicate the absolute configuration of those stereocenters. Therefore, the compound of formula (Ic) represents two isomers in total:

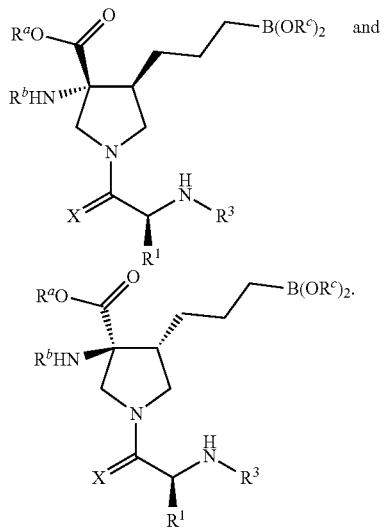

In certain embodiments, a therapeutic preparation of the compound of the invention may be enriched to provide predominantly one enantiomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, a therapeutic preparation may be enriched to provide predominantly one diastereomer of the compound of the invention. A diastereomerically enriched mixture may comprise, for example, at least 60 mol percent of one diastereomer, or more preferably at least 75, 90, 95, or even 99 mol percent.

In certain embodiments, the compounds of the invention exhibit an improved pharmacokinetic profile relative to existing arginase inhibitors.

In certain embodiments, the compounds of the invention exhibit improved bioavailability relative to existing arginase inhibitors.

Methods of Treatment

Several specific approaches to T-cell activation have shown considerable recent promise in the treatment of tumors. One such approach involves activation of T-cells by blockade of the T-cell surface antigen CTLA-4 by the antibody ipilimumab. A second approach is to prevent the activation of immune checkpoints by blocking the interaction of programmed cell death 1 protein, or PD-1, expressed on T-cells and its ligand, PD-L1 found on many tumors. A third approach is to activate the T-cell receptor by supplying key stimulating factors or nutrients such as tryptophan.

Inhibitors of indoleamine dioxygenase, or DO, have been shown to restore extracellular tryptophan without which the T-cell receptor cannot become active. Arginine, like tryptophan, is an amino acid that is fundamental to the function of cytotoxic T-cells. Without arginine, tumor-specific cytotoxic T-cells fail to express a functional T-cell receptor on their surface and as a result are unable to activate, proliferate, or mount an effective anti-tumor response. In response to tumor-secreted factors, myeloid-derived suppressor cells, or MDSCs, accumulate around the tumor and secrete the enzyme arginase, resulting in depletion of arginine from the tumor microenvironment.

Depletion of arginine due to elevated levels of arginase has been observed in renal cell carcinoma and acute myeloid leukemia. In addition, significant MDSC infiltrates have been observed in pancreatic, breast and other tumor types.

Certain embodiments of the present invention provide a method of treating cancer by increasing arginine levels in a tumor microenvironment, thereby allowing activation of the body's cytotoxic T-cells.

One means of increasing arginine levels in the tumor microenvironment is by inhibiting arginase. Inhibitors of arginase, such as the compounds of the invention, may promote an anti-tumor immune response by restoring arginine levels, thereby allowing activation of the body's cytotoxic T-cells.

Accordingly, in certain embodiments, the invention provides methods for treating or preventing cancer, comprising administering to a subject in need thereof a therapeutically effective amount of a compound of the invention (e.g., a compound of Formula I, Ia, Ib, Ic, Id, Ie, If, Ig, or Ih), or a pharmaceutical composition comprising said compound.

In certain embodiments, the cancer that is treated by the methods of the invention is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Extracranial Germ Cell Tumor, Extragonadal Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CIVIL), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Renal Pelvis Cancer, Ureter Cancer, Transitional Cell Cancer, Retinoblastoma, Rhabdomyosarcoma, Salivary Gland Cancer, Sarcoma, Sézary Syndrome, Skin Cancer, Small Cell Lung Cancer, Small Intestine Cancer, Soft Tissue Sarcoma, Squamous Cell Carcinoma, Squamous Neck Cancer with Occult Primary, Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Gestational Trophoblastic Tumor, Unknown Primary, Unusual Cancer of Childhood, Urethral Cancer, Uterine Cancer, Uterine Sarcoma, Waldenström Macroglobulinemia, or Wilms Tumor.

In certain embodiments, the cancer that is treated by the methods of the invention is a variety of acute myeloid leukemia (AML), bladder cancer, breast cancer, colorectal cancer, chronic myelogenous leukemia (CML), esophageal cancer, gastric cancer, lung cancer, melanoma, mesothelioma, non-small cell lung carcinoma (NSCLC), ovarian cancer, pancreatic cancer, prostate cancer, renal cancer, or skin cancer.

In certain embodiments, the cancer that is treated by the methods of the invention is a variety of acute myeloid leukemia (AML), breast cancer, colorectal cancer, chronic myelogenous leukemia (CML), esophageal cancer, gastric cancer, lung cancer, melanoma, non-small cell lung carcinoma (NSCLC), pancreatic cancer, prostate cancer, or renal cancer.

In certain embodiments, the cancer is selected from bladder cancer, breast cancer (including TNBC), cervical cancer, colorectal cancer, chronic lymphocytic leukemia (CLL), diffuse large B-cell lymphoma (DLBCL), esophageal adenocarcinoma, glioblastoma, head and neck cancer, leukemia (acute and chronic), low-grade glioma, lung cancer (including adenocarcinoma, non-small cell lung cancer, and squamous cell carcinoma), Hodgkin's lymphoma, non-Hodgkin lymphoma (NHL), melanoma, multiple myeloma (MM), ovarian cancer, pancreatic cancer, prostate cancer, renal cancer (including renal clear cell carcinoma and kidney papillary cell carcinoma), and stomach cancer.

Combination therapy is an important treatment modality in many disease settings, such as cancer. Recent scientific advances have increased our understanding of the pathophysiological processes that underlie these and other complex diseases. This increased understanding has provided impetus to develop new therapeutic approaches using combinations of drugs directed at multiple therapeutic targets to improve treatment response, minimize development of resistance, or minimize adverse events. In settings in which combination therapy provides significant therapeutic advantages, there is growing interest in the development of combinations with new investigational drugs, such as arginase inhibitors.

When considering the administration of multiple therapeutic agents together, one must be concerned about what sort of drug interactions will be observed. This action can be positive (when the drug's effect is increased) or antagonistic (when the drug's effect is decreased) or a new side effect can be produced that neither produces on its own.

When the interaction causes an increase in the effects of one or both of the drugs the interaction, the degree to which the final effect of the combined drugs is greater than administering either drug alone can be calculated resulting in what is called the "combination index" (CI) (Chou and Talalay, 1984). A combination index at or around 1 is considered "additive"; whereas a value greater than 1 is considered "synergistic".

The present invention provides methods for combination therapy in treating or preventing cancer comprising an arginase inhibitor (e.g., a compound of the invention) and one or more additional chemotherapeutic agents.

Certain embodiments of the invention relate to treating cancer comprising conjointly administering a chemotherapeutic agent and a compound of the invention.

In certain embodiments, the chemotherapeutic is an immune-stimulating agent. For example, the immune-stimulating agent may be a pro-inflammatory agent.

The chemotherapeutic agent that may be conjointly administered with the arginase inhibitors described herein in the methods of the invention include aminoglutethimide, amsacrine, anastrozole, asparaginase, AZD5363, Bacillus Calmette-Guérin vaccine (bcg), bicalutamide, bleomycin, bortezomib, buserelin, busulfan, campothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epacadostat, epirubicin, erlotinib, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, nilutamide, nocodazole, octreotide, olaparib, oxaliplatin, paclitaxel, pamidronate, pazopanib, pentostatin, perifosine, plicamycin, pomalidomide, porfimer, procarbazine, raltitrexed, rituximab, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, or vinorelbine.

In certain embodiments, the chemotherapeutic agent that may be administered with the arginase inhibitors described herein in the methods of the invention include abagovomab, adecatumumab, afutuzumab, anatumomab mafenatox, apolizumab, atezolizumab, blinatumomab, catumaxomab, durvalumab, epacadostat, epratuzumab, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab.

In certain embodiments, the chemotherapeutic agent is ipilimumab, nivolumab, pembrolizumab, or pidilizumab.

Many combination therapies have been developed for the treatment of cancer. In certain embodiments, compounds of the invention may be conjointly administered with a combination therapy. Examples of combination therapies with which compounds of the invention may be conjointly administered are included in Table 1.

TABLE 1

Exemplary combinatorial therapies for the treatment of cancer.

| Name | Therapeutic agents |
| --- | --- |
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |

TABLE 1-continued

Exemplary combinatorial therapies for the treatment of cancer.

| Name | Therapeutic agents |
| --- | --- |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |

TABLE 1-continued

Exemplary combinatorial therapies for the treatment of cancer.

| Name | Therapeutic agents |
|---|---|
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Flourouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, the conjointly administered chemotherapeutic agent is selected from a metabolic enzyme inhibitor, such as glucose transporters, hexokinase, pyruvate kinase M2, lactate dehydrogenase 1 or 2, pyruvate dehydrogenase kinase, fatty acid synthase and glutaminase. In some embodiments, the inhibitor inhibits lactate dehydrogenase 1 or 2, or glutaminase. In certain embodiments, the inhibitor is CB-839.

Immune-targeted agents (also known as immuno-oncology agents) act against tumors by modulating immune cells. The field of cancer immunotherapy is rapidly growing, with new targets constantly being identified (Chen and Mellman, 2013; Morrissey et al., 2016; Kohrt et al., 2016). The present invention provides a combination of an immuno-oncology agent and a glutaminase inhibitor.

Examples of immuno-oncology agents comprise agents that modulate immune checkpoints such as 2B4, 4-1BB (CD137), AaR, B7-H3, B7-H4, BAFFR, BTLA, CD2, CD7, CD27, CD28, CD30, CD40, CD80, CD83 ligand, CD86, CD160, CD200, CDS, CEACAM, CTLA-4, GITR, HVEM, ICAM-1, KIR, LAG-3, LAIR1, LFA-1 (CD11a/CD18), LIGHT, NKG2C, NKp80, OX40, PD-1, PD-L1, PD-L2, SLAMF7, TGFRβ, TIGIT, Tim3 and VISTA.

Immuno-oncology agents may be in the form of antibodies, peptides, small molecules or viruses.

In some embodiments, the conjointly administered chemotherapeutic agent is an immuno-oncology therapeutic agent, such as an inhibitor of arginase, CTLA-4, indoleamine 2,3-dioxygenase, and/or PD-1/PD-L1. In certain embodiments, the immuno-oncology therapeutic agent is abagovomab, adecatumumab, afutuzumab, alemtuzumab, anatumomab mafenatox, apolizumab, atezolizumab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, ocaratuzumab, ofatumumab, olatatumab, pembrolizumab, pidilizumab, rituximab, ticilimumab, samalizumab, or tremelimumab. Alternatively, the immuno-oncology therapeutic agent is abagovomab, adecatumumab, afutuzumab, anatumomab mafenatox, apolizumab, atezolizumab, blinatumomab, catumaxomab, durvalumab, epacadostat, epratuzumab, indoximod, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab. In some embodiments, the immuno-oncology agent is indoximod, ipilimumab, nivolumab, pembrolizumab, or pidilizumab. In certain embodiments, the immuno-oncology therapeutic agent is ipilimumab.

Exemplary immuno-oncology agents are disclosed in Adams, J. L. et al. "Big Opportunities for Small Molecules in Immuno-Oncology" *Nature Reviews Drug Discovery* 2015, 14, page 603-621, the contents of which are hereby incorporated by reference.

In certain embodiments, the conjointly administered chemotherapeutic agent is a pro-inflammatory agent. In certain embodiments, the pro-inflammatory agent administered with the arginase inhibitors of the invention is a cytokine or a chemokine.

Pro-inflammatory cytokines are produced predominantly by activated macrophages and are involved in the up-regulation of inflammatory reactions. Exemplary pro-inflammatory cytokines include IL-1, IL-10, IL-6, IL-8, TNF-α, and IFN-γ.

Chemokines are a group of small cytokines. Pro-inflammatory chemokines promote recruitment and activation of multiple lineages of leukocytes (e.g., lymphocytes, macrophages). Chemokines are related in primary structure and share several conserved amino acid residues. In particular, chemokines typically include two or four cysteine residues that contribute to the three-dimensional structure via formation of disulfide bonds. Chemokines may be classified in one of four groups: C—C chemokines, C—X—C chemokines, C chemokines, and C—X$_3$—C chemokines. C—X—C chemokines include a number of potent chemoattractants and activators of neutrophils, such as interleukin 8 (IL-8), PF4 and neutrophil-activating peptide-2 (NAP-2). The C—C chemokines include, for example, RANTES (Regulated on Activation, Normal T Expressed and Secreted), macrophage inflammatory proteins 1-alpha and 1-beta (MIP-1a and MIP-1β), eotaxin and human monocyte chemotactic proteins 1 to 3 (MCP-1, MCP-2, MCP-3), which have been characterized as chemoattractants and activators of monocytes or lymphocytes.

Accordingly, exemplary pro-inflammatory chemokines include MIP-1α, MIP-1β, MIP-1γ, MCP-1, MCP-2, MCP-3, IL-8, PF4, NAP-2, RANTES, CCL2, CCL3, CCL4, CCL5, CCL11, CXCL2, CXCL8, and CXCL10.

In certain embodiments, the method of treating or preventing cancer further comprises administering one or more non-chemical methods of cancer treatment, such as radiation therapy, surgery, thermoablation, focused ultrasound therapy, cryotherapy, or a combination of the foregoing.

Cellular pathways operate more like webs than superhighways. There are multiple redundancies, or alternate routes, that are activated in response to the inhibition of a pathway. This redundancy promotes the emergence of resistant cells or organisms under the selective pressure of a targeted agent, resulting in drug resistance and clinical relapse.

In certain embodiments of the invention, the chemotherapeutic agent is administered simultaneously with the arginase inhibitor. In certain embodiments, the chemotherapeutic agent is administered within about 5 minutes to within about 168 hours prior or after of the arginase inhibitor.

The present invention provides combination therapies comprising an immuno-oncology agent selected from inhibitors of CTLA-4, indoleamine 2,3-dioxygenase, and PD-1/PD-L1, and an arginase inhibitor of formula (I). In certain embodiments, the combination therapy treats or prevents cancer, an immunological disorder, or a chronic infection.

In certain embodiments, the invention provides methods for treating or preventing an immunological disease, comprising administering to a subject in need thereof a therapeutically effective amount of a compound of the invention (e.g., a compound of Formula I, Ia, Ib, Ic, Id, Ie, If, Ig, or Ih), or a pharmaceutical composition comprising said compound.

In certain embodiments, the immunological disease is selected from ankylosing spondylitis, Crohn's disease, erythema nodosum leprosum (ENL), graft versus host disease (GVHD), HIV-associated wasting syndrome, lupus erythematosus, organ transplant rejection, post-polycythemia, psoriasis, psoriatic arthritis, recurrent aphthous ulcers, rheumatoid arthritis (RA), severe recurrent aphthous stomatitis, systemic sclerosis, and tuberous sclerosis.

In certain embodiments, the method for treating or preventing an immunological disease further comprises conjointly administering an immuno-oncology therapeutic agent, as described above.

In certain embodiments, the invention provides methods for treating or preventing a chronic infection, comprising administering to a subject in need thereof a therapeutically effective amount of a compound of the invention (e.g., a compound of Formula I, Ia, Ib, Ic, Id, Ie, If, Ig, or Ih), or a pharmaceutical composition comprising said compound.

In certain embodiments, the chronic infection is selected from bladder infection, chronic fatigue syndrome, cytomegalovirus/epstein barr virus, fibromyalgia, hepatitis B virus (HBV), hepatitis C virus (HCV), HIV/AIDS virus, *mycoplasma* infection, and urinary tract infections.

In certain embodiments, the method for treating or preventing a chronic infection further comprises conjointly administering an immuno-oncology therapeutic agent, as described above.

Arginase plays multiple major roles within the body. In addition to modulating immune responses, arginase is involved in regulating nitric oxide levels effecting vasodilation and bronchodilation (Jung et al., 2010; Morris, 2010). Fibrosis and remodeling also relies on arginase activity that functions in upstream processes for proline, collagen and polyamine production (Kitowska et al., 2008; Grasemann et al., 2015).

In certain embodiments, the invention provides a method for the treatment or prevention of a disease or condition associated with expression or activity of arginase I, arginase II, or a combination thereof in a subject, comprising administering to the subject a therapeutically effective amount of at least one of formula (I), or a pharmaceutically acceptable salt or stereoisomer thereof.

In certain embodiments, the disease or condition is selected from cardiovascular disorders, sexual disorders, wound healing disorders, gastrointestinal disorders, autoimmune disorders, immune disorders, infections, pulmonary disorders and hemolytic disorders.

In certain embodiments, the disease or condition is a cardiovascular disorder selected from systemic hypertension, interstitial lung disease, pulmonary arterial hypertension (PAH), pulmonary arterial hypertension in high altitude, ischemia reperfusion (IR) injury, myocardial infarction, and atherosclerosis.

In certain embodiments, the disease or condition is pulmonary arterial hypertension (PAH).

In certain embodiments, the disease or condition is myocardial infarction or atherosclerosis.

In certain embodiments, the disease or condition is a pulmonary disorder selected from chemically-induced lung fibrosis, idiopathic pulmonary fibrosis, cystic fibrosis, chronic obstructive pulmonary disease (COPD), and asthma.

In certain embodiments, the disease or condition is an autoimmune disorder selected from encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

In certain embodiments, the disease or condition is an immune disorder selected from myeloid-derived suppressor cell (MDSC) mediated T-cell dysfunction, human immunodeficiency virus (HIV), autoimmune encephalomyelitis, and ABO mismatch transfusion reaction.

In certain embodiments, the disease or condition is myeloid-derived suppressor cell (MDSC) mediated T-cell dysfunction.

In certain embodiments, the disease or condition is a hemolytic disorder selected from sickle-cell disease, thalassemias, hereditary spherocytosis, stomatocytosis, microangiopathic hemolytic anemias pyruvate kinase deficiency, infection-induced anemia, cardiopulmonary bypass and mechanical heart valve-induced anemia, and chemical induced anemia.

In certain embodiments, the disease or condition is a gastrointestinal disorder selected from gastrointestinal motility disorders, gastric cancer, inflammatory bowel disease, Crohn's disease, ulcerative colitis, and gastric ulcer.

In certain embodiments, the disease or condition is a sexual disorder selected from Peyronie's Disease and erectile dysfunction.

In certain embodiments, the disease or condition is an infection selected from a parasitic infection, a viral infection, and a bacterial infection. In certain embodiments the bacterial infection is tuberculosis.

In certain embodiments, the disease or condition is ischemia reperfusion (IR) injury selected from liver IR, kidney IR, and myocardial IR.

In certain embodiments, the disease or condition is selected from renal disease inflammation, psoriasis, leishmaniasis, neurodegenerative diseases, wound healing, human immunodeficiency virus (HIV), hepatitis B virus (HBV), *H. pylori* infections, fibrotic disorders, arthritis, candidiasis, periodontal disease, keloids, adenotonsillar disease, African sleeping sickness and Chagas' disease.

In certain embodiments, the disease or condition is a wound healing disorder selected from infected and uninfected wound healing.

In further embodiments, the present invention provides a method of identifying a therapeutic agent effective to increase the level of arginine in a tumor, comprising:
a) measuring a first level of arginine in a tumor;
b) contacting the tumor with a therapeutic agent, such as a compound of formula (I); and
c) measuring a second level of arginine in the tumor;
wherein when the second level of arginine is higher than the first level of arginine, then the therapeutic agent is effective to increase the level of arginine in the tumor.

In certain embodiments, this method is conducted in vitro. In alternative embodiments, this method is conducted in vivo.

In certain embodiments (e.g., when the method is conducted in vivo), the step of contacting the tumor with a therapeutic agent comprising administering the therapeutic agent to a subject. In certain embodiments, the subject can be a human.

A level of arginine may be measured, for example, by HPLC, mass spectrometry, LCMS, or other analytic techiques known to those of skill in the art. The invention also provides a method of identifying a therapeutic agent effective to increase the level of arginine in a tumor in a subject, comprising:
a) measuring a first level of arginine in a tumor of a subject;
b) administering to the subject a therapeutic agent, such as a compound of formula (I); and
c) measuring a second level of arginine in the tumor of the subject;
   wherein when the second level of arginine is higher than the first level of arginine, then the therapeutic agent is effective to increase the level of arginine in the tumor of the subject.

In certain embodiments, the step of administering comprises oral administration of the therapeutic agent. Alternatively, the step of administering can comprise parenteral administration of the therapeutic agent. Further methods of administration are discussed herein.

In certain embodiments, the subject is a human.

As used herein, the term "in a tumor" refers to the entire tumor mass and the tumor microenvironment. For example, the tumor mass can include, but is in no way limited to, cancer (tumorous) cells, T-cells, macrophages, and stromal cells. The "tumor microenvironment" is an art-recognized term and refers to the cellular environment in which the tumor exists, and includes, for example, surrounding blood vessels, immune cells, other cells, fibroblasts, signaling molecules, and the extracellular matrix. Therefore, measurement of arginine "in a tumor" refers to measurement of arginine in the tumor mass or in its microenvironment.

Accordingly, in certain embodiments of the methods described herein, the first and second levels of arginine are measured in the tumor cells.

In other embodiments, the first and second levels of arginine are measured in stromal cells associated with the tumor.

In certain embodiments, the therapeutic agent is a compound of Formula (I). Exemplary compounds are described herein.

In certain embodiments in which the therapeutic agent is effective to increase the level of arginine in a tumor, the therapeutic agent can be effective to treat the tumor.

In other embodiments, the present invention provides a method of assessing a response of a tumor to an agent of arginine therapy, comprising:
a) measuring a first level of arginine in a tumor of a cancer patient;
b) administering to the patient an agent of arginine therapy; and
c) measuring a second level of arginine in the tumor of the patient, thereby assessing the response of the tumor to the agent of arginine therapy.

In certain embodiments, if the second level of arginine is higher than the first level of arginine, then the tumor is responsive to (i.e., is treated by) the agent of arginine therapy. An increase of arginine in a tumor mass or in the tumor microenvironment can indicate an increase in the number of cytotoxic T-cells or an increase in the activity of cytotoxic T-cells.

An "agent of arginine therapy" as used herein, means a therapeutic agent that can cause an increase in the level of arginine in the system of interest (e.g., a tumor mass and its microenvironment). Preferably, the agent of arginine therapy is an arginase inhibitor. More preferably, the arginase inhibitor is a compound of Formula (I).

In other embodiments, the present invention provides a method of assessing the anti-cancer efficacy of an agent of arginine therapy, comprising:
a) measuring a first level of arginine in a tumor of a cancer patient;
b) administering to the patient an agent of arginine therapy; and
c) measuring a second level of arginine in the tumor of the patient, thereby assessing the anti-cancer efficacy of an agent of arginine therapy.

In certain embodiments, when the second level of arginine is higher than the first level of arginine, then the agent of arginine therapy is efficacious for treating cancer in a patient.

In certain embodiments, the agent of arginine therapy is an arginase inhibitor.

The present invention also provides a method for treating or preventing cancer, comprising conjointly administering to a subject in need thereof a therapeutically effective amount of an agent of arginine therapy and one or more additional chemotherapeutic agents.

In certain embodiments, administering the agent of arginine therapy effects an increase in a level of arginine in a tumor of the subject relative to the level of arginine in the tumor prior to administration.

In certain embodiments, administering the agent of arginine therapy effects an increase in a level of arginine in the tumor cells of the subject relative to the level of arginine in the tumor cells prior to administration.

Similarly, administering the agent of arginine therapy may effect an increase in a level of arginine in stromal cells associated with the tumor of the subject relative to the level of arginine in the stromal cells prior to administration.

In certain embodiments, the agent of arginine therapy is an arginase inhibitor. A number of exemplary arginase inhibitors are described herein. In particular embodiments, the arginase inhibitor is a compound having the structure of any one of Formulae I, Ia, Ib, Ic, Id, Ie, If, Ig, or Ih, which are described herein.

In other embodiments, the invention provides methods for assessing the anti-cancer efficacy of a combination therapy regimen, comprising:
a) measuring a first level of arginine in a tumor of a cancer patient;
b) conjointly administering to the patient an agent of arginine therapy and one or more additional chemotherapeutic agents; and
c) measuring a second level of arginine in the tumor of the patient, thereby assessing the anti-cancer efficacy of the combination therapy regimen.

In certain embodiments, when the second level of arginine is higher than the first level of arginine, then the combination therapy regimen is efficacious for treating cancer in the patient.

In certain embodiments, the agent of arginine therapy used in the combination therapy regimen is an arginase inhibitor, such as a compound of any one of Formulae I, Ia, Ib, Ic, Id, Ie, If, Ig, or Ih.

In certain embodiments, the combination therapy regimen is more efficacious than a therapy regimen of the arginase inhibitor as a single agent, or a therapy regimen of the additional chemotherapeutic agent as a single agent.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing one or more hydrogens on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a guanidino, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

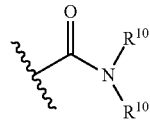

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

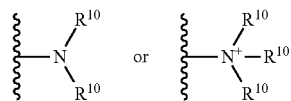

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

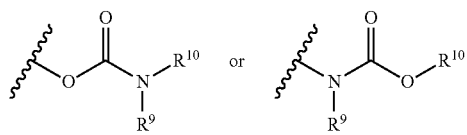

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be susbstituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "(cycloalkyl)alkyl", as used herein, refers to an alkyl group substituted with a cycloalkyl group.

The term "carbonate" is art-recognized and refers to a group —OCO2-10°, wherein $R^{10}$ represents a hydrocarbyl group.

The term "carboxy", as used herein, refers to a group represented by the formula —$CO_2H$.

The term "ester", as used herein, refers to a group —C(O)O$R^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "heteroaralkyl", as used herein, refers to an alkyl group substituted with a heteroaryl group.

The term "heteroalkyl", as used herein, refers to a saturated or unsaturated chain of carbon atoms and at least one heteroatom, wherein no two heteroatoms are adjacent.

The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocycloalkyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocycloalkyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocycloalkyl groups include, for example, piperidine, piperazine, pyrrolidine, morpholine, lactones, lactams, and the like.

The term "(heterocycloalkyl)alkyl", as used herein, refers to an alkyl group substituted with a heterocycloalkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

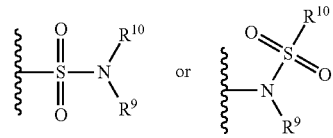

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

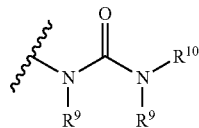

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

The term "dioxaborolane", as used herein, refers to a chemical group represented by the general formula:

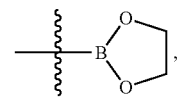

wherein the dioaxaborolane is optionally substituted at any substitutable position by one or more substituents including, but not limited to, alkyl (e.g., substituted alkyl), hydroxyalkyl, alkoxyl, carboxyalkyl, —COOH, aryl, heteroaryl, aralkyl, heteroaralkyl, etc. Alternatively, the dioxaborolane can be substituted at two adjacent substitutable positions, such that the two substituents, together with the intervening atoms, form an optionally substituted cycloalkyl or aryl ring (as in, e.g., catecholatoboron-).

The term "dioxaborolanone", as used herein, refers to a chemical group represented by the general formula:

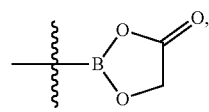

wherein the dioxaborolanone is optionally substituted at any substitutable position by one or more substituents including, but not limited to, alkyl (e.g., substituted alkyl), hydroxyalkyl, alkoxyl, carboxyalkyl, —COOH, aryl, heteroaryl, aralkyl, heteroaralkyl, etc.

The term "dioxaborolandione", as used herein, refers to a chemical group represented by the general formula:

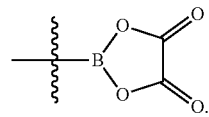

The term "dioxaborinane", as used herein, refers to a chemical group represented by the general formula:

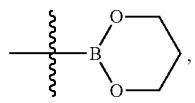

wherein the dioxaborinane is optionally substituted at any substitutable position by one or more substituents including, but not limited to, alkyl (e.g., substituted alkyl), hydroxyalkyl, alkoxyl, carboxyalkyl, —COOH, aryl, heteroaryl, aralkyl, heteroaralkyl, etc. Alternatively, the dioxaborinane can be substituted at two adjacent substitutable positions, such that the two substituents, together with the intervening atoms, form an optionally substituted cycloalkyl or aryl ring.

The term "dioxaborinanone", as used herein, refers to a chemical group represented by the general formula:

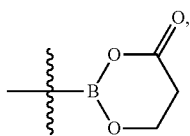

wherein the dioxaborinanone is optionally substituted at any substitutable position by one or more substituents including, but are not limited to, alkyl (e.g., substituted alkyl), hydroxyalkyl, alkoxyl, carboxyalkyl, —COOH, aryl, heteroaryl, aralkyl, heteroaralkyl, etc.

The term "dioxaborinandione", as used herein, refers to a chemical group represented by the general formula:

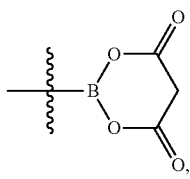

wherein the dioxaborinandione is optionally substituted at any substitutable position by one or more substituents including, but are not limited to, alkyl (e.g., substituted alkyl), hydroxyalkyl, alkoxyl, carboxyalkyl, —COOH, aryl, heteroaryl, aralkyl, heteroaralkyl, etc.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of Formula I, Ia, Ib, Ic, Id, Ie, If, Ig, or Ih). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. Alternatively, amides (e.g., an amide of an amino group) may be a prodrug of the invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

In other preferred embodiments, prodrugs of the invention encompass compounds in which the boronic acid is esterified or otherwise modified to form a boronic acid derivative capable of hydrolyzing under physiologic conditions to the parent boronic acid. For example, the compounds of the invention include tartrate or citrate "esters" of boronic acids, including where the boron forms a boracycle by bonding to two heteroatoms of the tartrate or citrate moiety. Analogously, the compounds of the invention include mandelic acid or oxalic acid esters of the parent boronic acids. Representative boronic acid esters are pictured below:

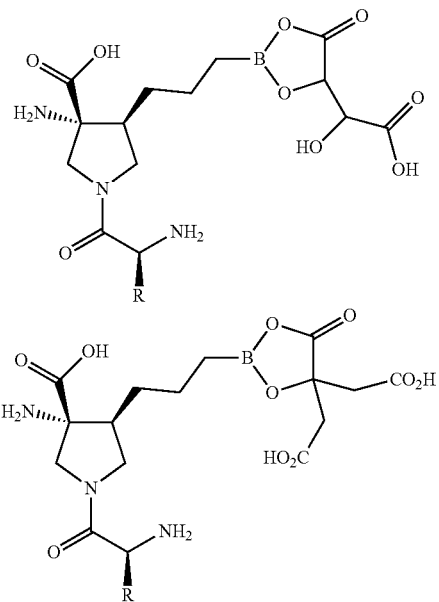

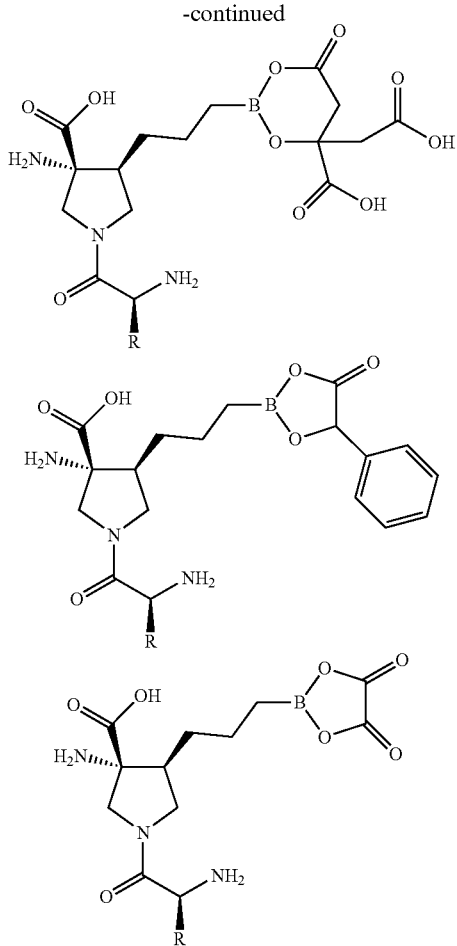

Pharmaceutical Compositions

In certain embodiments, the invention provides a pharmaceutical composition comprising a compound of the invention, such as a compound of formula I, Ia, Ib, Ic, Id, Ie, If, Ig, or Ih, or a pharmaceutically acceptable salt thereof; and a pharmaceutically acceptable carrier.

In certain embodiments, the present invention provides a pharmaceutical preparation suitable for use in a human patient, comprising any compound of the invention (e.g., a compound of formula I, Ia, Ib, Ic, Id, Ie, If, Ig, or Ih), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

One embodiment of the present invention provides a pharmaceutical kit comprising a compound of the invention, such as a compound of formula I, Ia, Ib, Ic, Id, Ie, If, Ig, or Ih, or a pharmaceutically acceptable salt thereof, and optionally directions on how to administer the compound.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In certain preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ (e.g., wheat germ), olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I, Ia, Ib, Ic, Id, Ie, If, Ig, or Ih) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, oxalic, mandelic and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I, Ia, Ib, Ic, Id, Ie, If, Ig, or Ih. As another example, the salt may comprise less than one inorganic or organic acid molecule per molecule of base, such as two molecules of compound of Formula I, Ia, Ib, Ic, Id, Ie, If, Ig, or Ih per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Example 1: Synthetic Methods

The scheme below and subsequect experimental procedures illustrates a general method that can be used to prepare examples included in the invention. Variations in the method may be preferable depending on the salt form desired. For example, if the hydrochloric acid salt is desired, intermediate 8 can be treated with hydrogen gas in the presence of palladium on carbon to give intermediate amino acid 9. Subsequent treatment with aqueous hydrochloric acid gives the target arginase inhibitor 10 as the hydrochloric acid salt.

If the free-base is desired, intermediate 8 can be used in a modified procedure. Here, treatment with trifluoroacetic acid followed by isobutylboronic acid gives intermediate amine 12. Subsequent reduction of the azide and deprotection of the benzyl ester using hydrogen gas in the presence of palladium on carbon gives target arginase ingibitor 13 as a free-base. A detailed description of these methods is provided below.

Synthesis of (3R,4S)-3-amino-1-((S)-2-aminopropanoyl)-4-(3-boronopropyl)pyrrolidine-3-carboxylic acid, dihydrochloride salt (10)

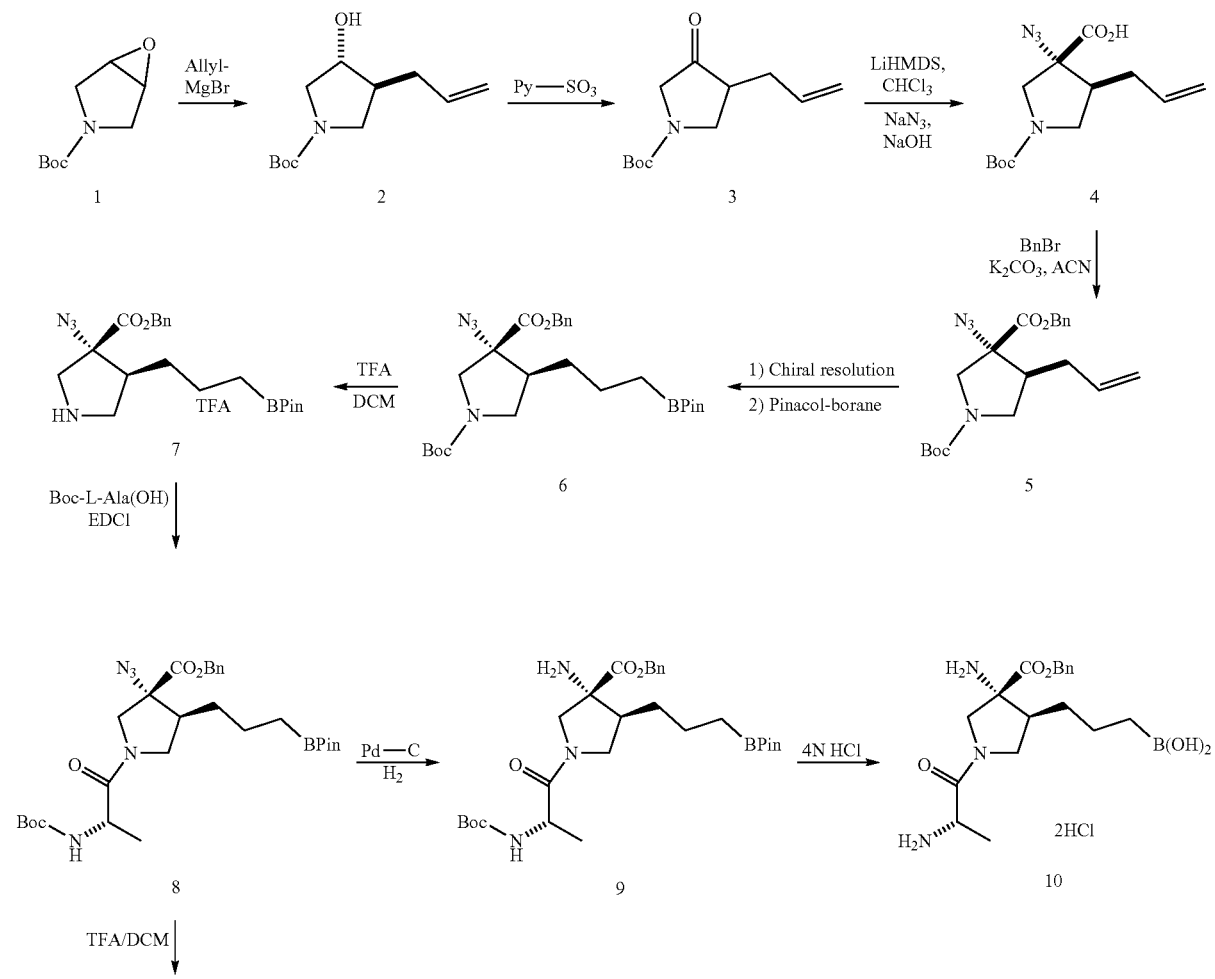

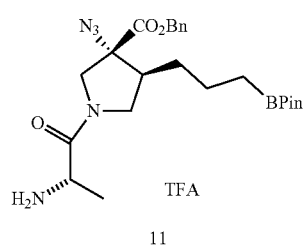 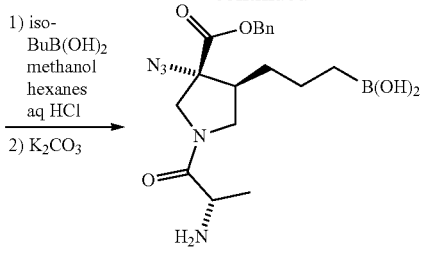 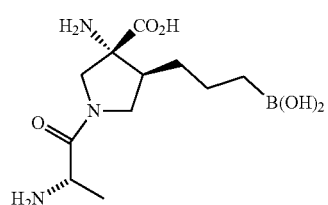

Step 1: Synthesis of tert-Butyl-trans-3-allyl-4-hydroxypyrrolidine-1-carboxylate (2, Racemic)

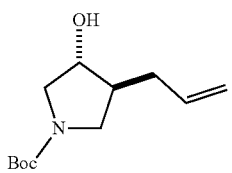

Allyl magnesium bromide (1,037 mL, 713 mmol, 0.69 M in diethyl ether) was cooled to 0° C. and carefully treated with tert-butyl 6-oxa-3-azabicyclo[3.1.0]hexane-3-carboxylate (60 g, 323.9 mmol) in anhydrous diethyl ether (324 mL, 1 M). After the addition was complete, the reaction mixture was stirred for 15 min, slowly quenched with saturated aqueous ammonium chloride (500 mL), extracted with diethyl ether (2×400 mL), dried over MgSO$_4$, filtered and concentrated. Purification by flash column chromatography (20-40% ethyl acetate in heptane) gave tert-butyl-trans-3-allyl-4-hydroxypyrrolidine-1-carboxylate (2, 64.33 g, 87% yield) as a pale yellow oil. $^1$H-NMR (CDCl$_3$, 400 MHz): $\delta_H$: 5.80 (1H, m), 5.06 (2H, m), 4.07 (1H, m), 3.57 (2H, m), 3.22 (1H, m), 3.08 (1H, m), 2.26-2.10 (2H, m) and 1.45 (9H, s).

Step 2: Synthesis of tert-Butyl-3-allyl-4-oxopyrrolidine-1-carboxylate (3, Racemic)

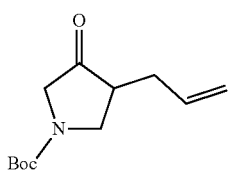

While under an atmosphere of dry nitrogen, an ice-cooled solution of tert-butyl-trans-3-allyl-4-hydroxypyrrolidine-1-carboxylate (2, 60 g, 264 mmol) and diisopropylethylamine (132.2 mL, 799.8 mmol) in dichloromethane (750 mL, 0.35 M) was treated dropwise with a solution of sulfur trioxide pyridine complex (94.95 g, 596.6 mmol) in anhydrous DMSO (750 mL) at a rate to keep the reaction mixture below 10° C. After the addition was complete, the mixture was stirred at 3° C. for 15 min, quenched with water (380 mL) and extracted with ethyl acetate (500 mL, then 2×300 mL). The combined organic solution was washed twice with water (200 mL), once with saturated aqueous sodium chloride (200 mL), dried (MgSO$_4$) and concentrated. The resulting crude oil was distilled at 105° C. (0.4 mm Hg) to afford tert-butyl 3-allyl-4-oxopyrrolidine-1-carboxylate (3, 58 g, 83% yield) as a colorless oil. $^1$H-NMR (CDCl$_3$, 400 MHz): $\delta_H$: 5.74 (1H, m), 5.09 (2H, m), 4.02 (1H, m), 3.88 (1H, d, J=19.4 Hz), 3.68 (1H, d, J=19.4 Hz), 3.31 (1H, dd, J=9.4, 8.3 Hz), 2.65 (1H, m), 2.54 (1H, m), 2.18 (1H, m) and 1.45 (9H, s).

Step 3: Synthesis of trans-4-Allyl-3-azido-1-(tert-butoxycarbonyl)pyrrolidine-3-carboxylic Acid (4, Racemic)

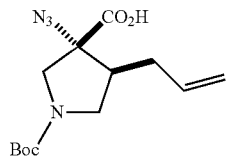

A solution of chloroform (26.86 mL, 333 mmol) and TMS-Cl (32.86 mL, 257.1 mmol) in anhydrous THF (300 mL) was cooled to −78° C. After stirring for 10 min, LHMDS (1M in THF, 249 mL, 249 mmol) was added at a rate such that the temperature remained below −60° C. (approximately 30 min). After stirring an additional 30 min at −60 to −70° C. (reaction mixture becomes cloudy) the solution was warmed to −20° C. (reaction mixture becomes clear) and treated with tert-butyl-3-allyl-4-oxopyrrolidine-1-carboxylate (3, 30 g, 133.2 mmol) in DMF (90 mL) and tetrabutylammonium acetate (3.69 g, 12.24 mmol) in DMF (90 mL) at a rate such that the internal reaction temperature remained below −20° C. (reaction becomes cloudy). After the addition was complete, the reaction mixture was warmed to room temperature with stirring until the ketone starting material was consumed (by TLC), then poured into saturated aqueous NH$_4$C$_1$ and extracted with EtOAc (3×100 mL). The combined organic layers were washed successively with saturated aqueous NH$_4$C$_1$ and saturated aqueous NaCl (2×80 mL), dried over MgSO$_4$, filtered and concentrated.

While under nitrogen, the crude TMS protected intermediate was dissolved in dry THF (300 mL), cooled to 0° C. and carefully treated with acetic acid (7.5 mL, 130.9 mmol) and TBAF (1 M in THF, 133.2 mL, 133.2 mmol) dropwise. After the reaction was complete, the reaction was stirred an additional 10 min at 0° C. then poured into saturated aqueous NaHCO$_3$ and extracted with EtOAc (3×100 mL).

The combined organic layers were washed with saturated aqueous NaCl, dried over MgSO$_4$, filtered and concentrated to afford the crude alcohol intermediate.

The crude alcohol was dissolved in dioxane (200 mL), cooled to 0° C., and treated with a pre-cooled (0° C.) solution of sodium azide (14.04 g, 399.5 mmol) and NaOH (15.98 g, 399.5 mmol) in water (200 mL) dropwise. The resulting reaction mixture was allowed to warm to room temperature with stirring overnight then quenched with of saturated aqueous NH$_4$C$_1$ and was extracted with EtOAc (500 mL). The aqueous layer was separated and extracted with EtOAc (2×300 mL). The combined organic layers were washed with water and saturated aqueous NaCl, dried over MgSO$_4$, filtered and concentrated to give crude trans-4-allyl-3-azido-1-(tert-butoxycarbonyl)pyrrolidine-3-carboxylic acid (4, crude 45 g) which was used without further purification. $^1$H-NMR (CDCl$_3$, 400 MHz): δ$_H$: 5.80 (1H, m), 5.06 (2H, m), 4.05 (1H, dd, J=9.9, 4.9 Hz), 3.59 (2H, m), 3.22 (1H, dd, J=11.6, 4.4 Hz), 3.08 (1H, dd, J=11.0, 5.2 Hz), 2.24-2.04 (2H, m), 1.65 (1H, br s, OH) and 1.45 (9H, s).

Step 4: Synthesis of trans-3-Benzyl-1-(tert-butyl)-4-allyl-3-azidopyrrolidine-1,3-dicarboxylate

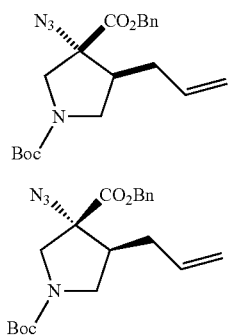

A solution of crude trans-4-allyl-3-azido-1-(tert-butoxycarbonyl)pyrrolidine-3-carboxylic acid (4, 39.5 g, 133 mmol-calculated quantity assuming 100% yield from previous steps) and K$_2$CO$_3$ (92.04 g, 666 mmol) in acetonitrile (317 mL) was cooled to 0° C. and treated with benzyl bromide (17.52 mL, 146.5 mmol). After stirring overnight at room temperature the solution was concentrated, dissolved in EtOAc (600 mL), washed with saturated aqueous NaCl, dried over MgSO$_4$, filtered and concentrated. Purification via silica gel chromatography (10 to 30% EtOAc in hexane) gave trans-3-benzyl-1-(tert-butyl)-4-allyl-3-azidopyrrolidine-1,3-dicarboxylate as yellow liquid (5, 40 g, 78% yield).

The product was separated into its enantiomers using a Chiral Technologies Chiralpak ADH column with isopropyl alcohol and hexanes (2:98) as an eluent. Analysis of the separated enantiomers using an analytical Chiralpak ADH column (4.6×250 mm) with the same eluent and a flow rate of 1.0 mL/min and UV detection (210 nm) gave the desired enantiomer (3-benzyl-1-(tert-butyl) (3R,4S)-4-allyl-3-azidopyrroli dine-1,3-dicarboxylate, 5a) with a retention time of 13.5 min and the undesired enantiomer (3-benzyl-1-(tert-butyl) (3S,4R)-4-allyl-3-azidopyrrolidine-1,3-dicarboxylate, 5b) at 10.3 min, each with an enantiomeric excess of approximately 98%. $^1$H-NMR (CDCl$_3$, 400 MHz): δ$_H$: 7.37 (5H, s), 5.62 (1H, m), 5.25 (2H, m), 5.00 (2H, m), 3.88 (1H, dd, J=37.2, 12.0 Hz), 3.58 (1H, ddd, J=37.2, 11.0, 7.0 Hz), 3.42 (1H, dd, J=21.4, 12.0 Hz), 3.28 (1H, ddd, J=28.3, 11.0, 5.4 Hz), 2.41 (1H, m), 2.11 (1H, m), 1.80 (1H, m) and 1.44 (9H, s).

Step 5: Synthesis of (3R,4S)-3-Benzyl 1-tert-butyl 3-azido-4-(3-(4,4,5,5-tetramethyl-1,3,2-dioxaborolan-2-yl)propyl)pyrrolidine-1,3-dicarboxylate (6)

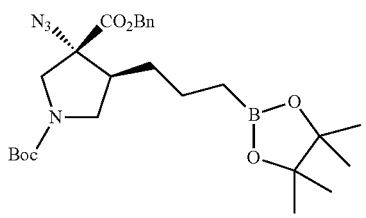

A stirred solution of 3-benzyl-1-(tert-butyl) (3R,4S)-4-allyl-3-azidopyrrolidine-1,3-dicarboxylate (5a, 16.4 g, 42.4 mmol) in anhydrous methylene chloride (130 mL), under an atmosphere of nitrogen, was treated with bis(1,5-cyclooctadiene)diiridium(I) dichloride (0.75 g, 1.12 mmol) and 1,2-bis(diphenylphosphino)ethane (0.894 g, 2.24 mmol) and the reaction was stirred for 30 minutes at room temperature and then cooled to −25° C. 4,4,5,5-tetramethyl[1,3,2]dioxaborolane (9.83 mL, 67.75 mmol) was added dropwise and then the reaction was allowed to slowly warm to room temperature and stirred for 20 hrs. Water (60 mL) was added and the reaction was stirred for 10 minutes, and then the methylene chloride was removed under reduced pressure. The remaining aqueous phase was extracted with ethyl acetate (3×100 mL). The combined organic phase was washed with brine, dried over anhydrous magnesium sulfate, filtered and concentrated in vacuo. The residual solid was passed through a short pad of silica gel, eluting with 15% to 30% ethyl acetate in hexane, to give (3R,4S)-3-benzyl 1-tert-butyl 3-azido-4-(3-(4,4,5,5-tetramethyl-1,3,2-dioxaborolan-2-yl)propyl)pyrrolidine-1,3-dicarboxylate (6, 12.5 g, 57%). $^1$H-NMR (CDCl$_3$, 400 MHz): δ$_H$: 7.35 (5H, m), 5.23 (2H, m), 3.85 (1H, dd, J=39.3, 11.8 Hz), 3.60 (1H, m), 3.37 (1H, dd, J=24.3, 11.8 Hz), 3.25 (1H, ddd, J=40, 10.6, 6.6 Hz), 2.33 (1H, m), 1.43 (9H, s), 1.39-1.26 (3H, m), 1.21 (12H, s), 1.07 (1H, m) and 0.68 (2H, m).

Step 6: Synthesis of (3R,4S)-3-Benzyl-3-azido-4-(3-(4,4,5,5-tetramethyl-1,3,2-dioxaborolan-2-yl) propyl)pyrrolidine-3-carboxylate, trifluoroacetic acid salt (7)

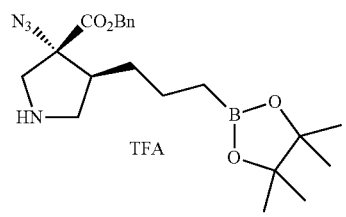

A solution of (3R,4S)-3-benzyl 1-tert-butyl 3-azido-4-(3-(4,4,5,5-tetramethyl-1,3,2-dioxaborolan-2-yl)propyl)pyrrolidine-1,3-dicarboxylate (6, 10.2 g, 19.8 mmol) was dissolved in anhydrous methylene chloride (160 mL), cooled to 0° C. and treated with trifluoroacetic acid (40 mL). The reaction mixture was then allowed to warm, stirred at room temperature for 4 hr and then concentrated under reduced pressure to give a viscous oil. The resultant oil was azeotroped with dry toluene (3×100 mL) to remove residual trifluoroacetic acid and then dried under high vacuum to give (3R,4S)-3-benzyl-3-azido-4-(3-(4,4,5,5-tetramethyl-1,3,2-dioxaborolan-2-yl)propyl)pyrrolidine-3-carboxylate, trifluoroacetic acid salt (7) as a very viscous oil (10.56 g), which slowly turns to a glass. $^1$H-NMR (CDCl$_3$, 400 MHz): $\delta_H$: 9.7 (1H, br m (exch), NH), 7.55 (1H, br s (exch), NH), 7.38 (5H, m), 5.31 (1H, d, J=11.7 Hz), 5.26 (1H, d, J=11.7 Hz), 3.77 (1H, d, J=12.5 Hz), 3.65 (1H, dd, J=11.8, 7.8 Hz), 3.32 (1H, d, J=12.4 Hz), 3.18 (1H, m), 2.54 (1H, m), 1.45-1.26 (3H, m), 1.22 (12H, s), 1.02 (1H, m) and 0.63 (2H, t, J=7.4 Hz).

Step 7: Synthesis of (3R,4S)-3-Benzyl-3-azido-K(S)-2-((tert-butoxylcarbonyl)amino)propanyoyl)-4-(3-(4,4,5,5-tetramethyl-1,3,2-dioxaborolan-2-yl)propyl)pyrrolidine-3-carboxylate (8)

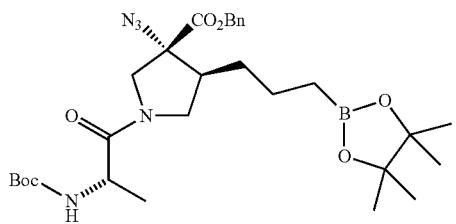

To a stirred solution of (3R,4S)-3-benzyl-3-azido-4-(3-(4,4,5,5-tetramethyl-1,3,2-dioxaborolan-2-yl)propyl)pyrrolidine-3-carboxylate, trifluoroacetic acid salt (7, 10.56 g, 19.8 mmol) in anhydrous methylene chloride (150 mL) was added DMAP (50 mg, catalytic) and HOBt (50 mg, catalytic) and N-(tert-butoxycarbonyl)-L-alanine (5.62 g, 29.7 mmol). The reaction was cooled to 0° C. under an atmosphere of dry nitrogen and then treated with EDCI (5.69 g, 29.7 mmol) and triethylamine (8.3 mL, 59.4 mmol). The reaction was stirred at 0° C. for 1 hr and then allowed to warm to room temperature and stirred for 16 hrs at this temperature. The reaction was poured into water (100 mL), stirred for 20 mins and then the phases were separated. The aqueous phase was extracted with 3×50 mL methylene chloride. The combined organic phase was washed with water, 1 N hydrochloric acid and brine, then dried over anhydrous magnesium sulfate, filtered and concentrated in vacuo. The residual oil was passed through a pad of silica gel, eluting with 5% to 50% ethyl acetate in hexanes, to give (3R,4S)-3-benzyl-3-azido-1-((S)-2-((tert-butoxylcarbonyl)amino)propanyoyl)-4-(3-(4,4,5,5-tetramethyl-1,3,2-dioxaborolan-2-yl)propyl)pyrrolidine-3-carboxylate (8) as a colorless oil (9.50 g, 82%), seen as a 1:1 mixture of rotamers by NMR at room temperature; $^1$H-NMR (CDCl$_3$, 400 MHz): $\delta_H$:7.56 (5H, m), 5.40 (0.5H, d, J=8.0 Hz, NH) and 5.34 (0.5H, d, J=8.0 Hz, NH), 5.29-5.19 (2H, m), 4.39 (0.5H, dq, J=7.2, 7.0 Hz) and 4.30 (0.5H, dq, J=7.2, 7.0 Hz), 4.06 (0.5H, d, J=13.0 Hz) and 3.89 (0.5H, d, J=11.1 Hz), 3.81 (0.5H, dd, J=12.0, 7.3 Hz) and 3.69 (0.5H, J=10.0, 7.0 Hz), 3.61 (0.5H, d, J=11.1 Hz) and 3.47 (0.5H, d, J=13.0 Hz), 3.54 (0.5H, dd, J=10.0, 6.0 Hz) and 3.33 (0.5H, dd, J=12.0, 6.3 Hz), 2.41 (1H, m), 1.43 (4.5H, s) and 1.42 (4.5H, s), 1.40-1.28 (3H, m), 1.31 (1.5H, d, J=6.8 Hz) and 1.20 (1.5H, J=6.8 Hz), 1.22 (12H, s), 1.04 (1H, m) and 0.67 (2H, m).

Step 8: Synthesis of (3R,4S)-3-amino-1-((S)-2-((tert-butoxylcarbonyl)amino)propanyoyl)-4-(3-(4,4,5,5-tetramethyl-1,3,2-dioxaborolan-2-yl)propyl)pyrrolidine-3-carboxylic Acid (9)

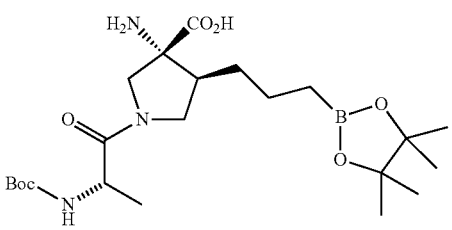

(3R,4S)-3-benzyl-3-azido-1-((S)-2-((tert-butoxylcarbonyl)amino)propanyoyl)-4-(3-(4,4,5,5-tetramethyl-1,3,2-dioxaborolan-2-yl)propyl)pyrrolidine-3-carboxylate (8, 9.48 g, 16.2 mmol) was dissolved in a 1:1 mixture of ethyl acetate and ethanol (120 mL). 10% Palladium on charcoal (500 mg) was added and the solution was degassed under vacuum and purged with hydrogen (hydrogen balloon). This purging procedure was repeated 3× and then the reaction was stirred under a hydrogen atmosphere for 5 hours. The reaction was placed back under vacuum to remove the residual hydrogen and then filtered through a pad of celite, with 4×30 mL ethanol washes. The solution was concentrated to ~20 mL under vacuum and then filtered through a 4µ syringe filter to remove traces of palladium. The solution was concentrated to dryness under vacuum and used without further purification. LC-MS: ESI+ (0.1% HCOOH in IPA/water): m/z for C$_{22}$H$_{40}$BN$_3$O$_7$: expected 469.3, observed 492.3 (M+Na)$^+$, 470.3 (M+H)$^+$, 414.2 (M+H−$^i$Bu)$^+$, 370.3 (M+H-Boc)$^+$, ESI−: 468.0 (M−H)$^-$.

Step 9: Synthesis of (3R,4S)-3-Amino-1-((S)-2-aminopropanyoyl)-4-(3-boronopropyl)pyrrolidine-3-carboxylic Acid, dihydrochloride Salt (10)

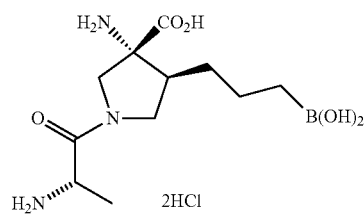

A suspension of (3R,4S)-3-amino-1-((S)-2-((tert-butoxylcarbonyl)amino)propanyoyl)-4-(3-(4,4,5,5-tetramethyl-1,3,2-dioxaborolan-2-yl)propyl)pyrrolidine-3-carboxylic acid (from the previous step) in 4N hydrochloric acid (50 mL) was stirred at 50° C. for 16 hrs and then cooled to room temperature. The reaction was diluted with a further 50 mL of water and then washed 5× with methylene chloride. The aqueous phase was concentrated to dryness under reduced pressure, keeping the water bath at or below 50° C. The resultant oil was dissolved in water (30 mL) and concentrated. This procedure was repeated 2× with further 30 mL aliquots of water and then dried under vacuum to give a pale yellow foam.

Dowex 550A-UPW hydroxide resin (75 g) was washed with water, methanol (2×) and water and then suction dried. The foam residue from the hydrolysis reaction was dissolved in water (100 mL) and treated with the washed Dowex resin (75 g), and stirred for 60 min, until a sample of the aqueous solution no longer tested positive with ninhydrin stain. The mixture was filtered and the resin washed successively with water, methanol, methylene chloride, methanol, methylene chloride, methanol, and finally water and suction dried briefly.

The resin was then stirred with 2N hydrochloric acid (50 mL) for 15 min and the aqueous decanted into a fritted funnel/filter flask and saved. This was repeated three times with 2N hydrochloric acid (3×50 mL), and the last resin stir was filtered and rinsed with water (20 mL). The combined aqueous filtrate was concentrated in vacuo and the residual foam dissolved three times in water (20 mL) and concentrated in order to remove residual HCl.

The off-white foamy solid was then dissolved in 30 mL water, frozen at −78° C. and lyophilized to dryness (36 hrs) to afford the product, (3R,4S)-3-amino-1-((S)-2-aminopropanyoyl)-4-(3-boronopropyl)pyrrolidine-3-carboxylic acid, dihydrochloride salt (10) as its dihydrochloride salt, as an off-white powder (4.90 g, 84% over 2 steps). The final compound was obtained as a 3:2 mixture of rotamers, at room temperature. $^1$H-NMR (D$_2$O, 400 MHz): $\delta_H$: 4.16-4.04 (1.6H, m), 3.95 (0.4H, m), 3.85 (0.6H, m), 3.68 (0.4H, m), 3.47-3.35 (1.6H, m), 3.18 (0.4H, m), 2.58 (0.6H, m) and 2.47 (0.4H, m), 1.52 (1H, m), 1.38 (1.2H, d, J=7.3 Hz) and 1.34 (1.8H, d, J=7.0 Hz), 1.32-1.09 (3H, m) and 0.64 (2H, m). LC-MS: ESI+ (0.1% HCOOH in IPA/water): m/z for $C_{11}H_{22}BN_3O_5$: expected 287.2, observed 288.2 (M+H)$^+$, 270.2 (M+H−H$_2$O)$^+$, 252.2 (M+H−2H$_2$O)$^+$, ESI−: 268.2 (M−H−H$_2$O)$^−$.

Synthesis of (3R,4S)-3-amino-1-((S)-2-aminopropanoyl)-4-(3-boronopropyl)pyrrolidine-3-carboxylic Acid (13)

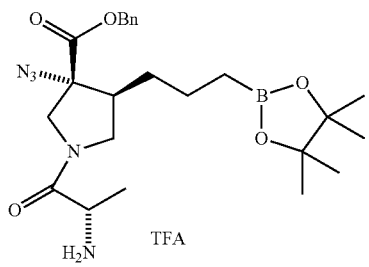

11

Step 1: Synthesis of (3R,4S)-benzyl-1-((S)-2-aminopropanoyl)-3-azido-4-(3-(4,4,5,5-tetramethyl-1,3,2-dioxaborolan-2-yl)propyl)pyrrolidine-3-carboxylate, TFA Salt (11)

A solution of (3R,4S)-benzyl-3-azido-1-((S)-2-((tert-butoxycarbonyl)amino)propanoyl)-4-(3-(4,4,5,5-tetramethyl-1,3,2-dioxaborolan-2-yl)propyl)pyrrolidine-3-carboxylate (30.04 g, 51.31 mmol) in anhydrous dichloromethane (250 mL) was cooled to 0° C. and then a solution of TFA (50 mL) in dichloromethane (50 mL) was added drop wise over 10 minutes. The solution was allowed to warm to room temperature and then stirred at this temperature for 3 hours, until TLC showed complete consumption of the starting material. The reaction mixture was concentrated in vacuo to give a pale yellow oil. This oil was dissolved in toluene (100 mL) and concentrated. The azeotropic procedure was repeated three times, to give the product (11), as the TFA salt, (30.85 g) as a pale yellow oil. $^1$H-NMR (400 MHz, D4-MeOH) δ: 7.39 (4H, m), 7.15 (1H, m), 5.29 (2H, dd, J=14, 12 Hz), 4.25-3.20 (5H, m), 2.51 (1H, m), 1.50-1.25 (6H, including 1.47 (1.5H, d, J=7.0 Hz) and 1.31 (1.5H, d, J=6.9 Hz (alanine rotamers))), 1.20 (12H, s)), 1.07 (1H, m) and 0.65 (2H, m). LCMS (ESI+ve): $C_{24}H_{36}BN_5O_5$ m/z calculated 485.3, found 486.2 (MW).

Step 2: synthesis of (3-((3S,4R)-1-((S)-2-aminopropanoyl)-4-azido-4-((benxyloxy)carbonyl)pyrrolodin-3-yl)propyl)boronic Acid, hydrochloride Salt

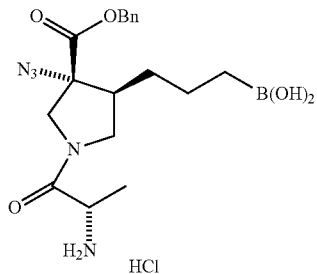 [SMILES: C[C@H](N)C(=O)N1C[C@H](CCCB(O)O)[C@](N=[N+]=[N-])(C(=O)OCc2ccccc2)C1 ; Cl]

The TFA salt of (3R,4S)-benzyl-1-((S)-2-aminopropanoyl)-3-azido-4-(3-(4,4,5,5-tetramethyl-1,3,2-dioxaborolan-2-yl)propyl)pyrrolidine-3-carboxylate (30.76 g, 51.31 mmol), was dissolved in a biphasic mixture of methanol (200 mL) and hexane (400 mL). Isobutylboronic acid (18.31 g, 179.6 mmol) and then 2N Hydrochloric acid (50.85 mL, 101.7 mmol) was added. The reaction mixture was stirred vigorously at room temperature for 16 hours. The methanol phase was separated and washed with hexane (5×100 mL) and then concentrated in vacuo to give the boronic acid, as the hydrochloride salt, as an off-white foam. $^1$H-NMR (400 MHz, D$_2$O) δ: 7.48-7.42 (5H, m), 5.31 (2H, m), 4.22 (1H, dd, J=13, 6.5 Hz), 3.95-3.10 (4H, m), 2.71-2.51 (1H, m), 1.40-1.25 (3H, m), 1.25-0.98 (4H, m including 1.20 (1.5H, d, J=6.9 Hz) and 1.07 (1.5H, d, J=6.9 Hz (alanine rotamers))) and 0.69 (2H, m). LCMS (ESI+ve): $C_{18}H_{26}BN_5O_5$ m/z calculated 403.2, found 404.2 (MH$^+$).

Step 3: synthesis of (3-((3S,4R)-1-((S)-2-aminopropanoyl)-4-azido-4-((benxyloxy)carbonyl)pyrrolodin-3-yl)propyl)boronic Acid (12)

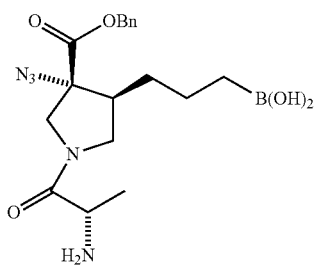

12

The hydrochloride salt of (3-((3S,4R)-1-((S)-2-aminopropanoyl)-4-azido-4-((benxyloxy)carbonyl)pyrrolodin-3-yl)propyl)boronic acid, from the previous step, was dissolved in 30 mL water and then the pH of the solution was adjusted to pH 9 by the careful addition of solid potassium carbonate. The resultant solution was saturated with the addition of solid sodium chloride and then was extracted with dichloromethane (5×100 mL). The combined dichloromethane phase was dried over magnesium sulfate, filtered and concentrated in vacuo to give the product (12), as its free base, as a white foamy solid (19.4 g, 48.11 mmol, 94%). $^1$H-NMR (400 MHz, D4-MeOH) δ: 7.44-7.36 (5H, m), 5.31 (1H, d, J=1.8 Hz), 5.27 (1H, d, J=1.8 Hz) 4.05 (1H, dd, J=12, 5 Hz), 3.80 (1H, m), 3.69-3.55 (2H, m), 3.45-3.30 (1H, m), 2.51 (1H, m), 1.40-1.05 (7H, m, including 1.22 (1.5H, d, J=6.8 Hz) and 1.07 (1.5H, d, J=6.8 Hz (alanine rotamers))) and 0.63 (2H, m). LCMS (ESI+ve): $C_{18}H_{26}BN_5O_5$ m/z calculated 403.2, found 404.7 (MH$^+$).

Step 4: synthesis of (3R,4S)-3-amino-1-((S)-2-aminopropanoyl)-4-(3-boronopropyl)-yl)pyrrolidine-3-carboxylate (13)

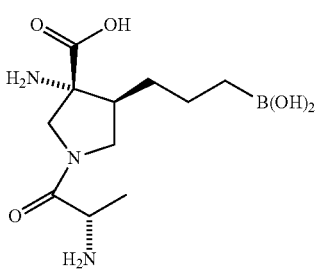

13

The azido benzyl ester, (3-((3S,4R)-1-((S)-2-aminopropanoyl)-4-azido-4-((benxyloxy)carbonyl)pyrrolodin-3-yl)propyl)boronic acid (9.70 g, 24.06 mmol) was suspended in a mixture of water (300 mL) and ethyl acetate (30 mL) and stirred vigorously. 10% Palladium on charcoal (2.6 g, 0.1 eq) was added and then the stirred mixture was evacuated under mild vacuum, and flushed with hydrogen. The evacuation/flushing procedure was repeated 3× to remove air and exchange it with hydrogen and then the reaction was stirred vigorously overnight at room temperature under a hydrogen balloon, at which time, LCMS analysis of a filtered aliquot showed the complete reduction of the azide and benzyl ester groups. The reaction mixture was put under vacuum to remove hydrogen and then flushed with nitrogen, filtered through a pad of celite (with 3 water washes) and then the solution was concentrated to approx 50 mL in vacuo. The resultant aqueous solution was filtered through a 4 micron filter (to remove trace Pd) and then concentrated in vacuo to give the title compound (13) as a white powder (6.45 g, 93%). $^1$H-NMR (400 MHz, D$_2$O) δ: 4.12 (1H, m), 4.05 (1H, m), 3.92 (1H, m), 3.60-3.22 (2H, m), 2.47-2.18 (1H, m), 1.58-1.31 (6H, m including 1.46 (3H, d, J=6.9 Hz)), 1.24-1.19 (1H, m) and 0.79 (2H, m). LCMS (ESI+ve): $C_{11}H_{20}BN_3O_5$ m/z calculated 287.2, found 269.9 (MH$^+$–H$_2$O), 251.9 (MH$^+$–2H$_2$O) and (ESI–ve): $C_{11}H_{20}BN_3O_5$ m/z calculated 287.2, found 267.7 (M–H–H$_2$O).

(3R,4S)-3-Amino-1-((S)-2-amino-3-methylbutanoyl)-4-(3-boronopropyl)pyrrolidine-3-carboxylic Acid, dihydrochloride (14)

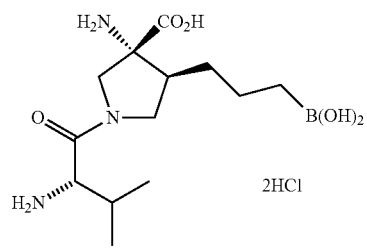

14

(3R,4S)-3-amino-1-((S)-2-amino-3-methylbutanoyl)-4-(3-boronopropyl)pyrrolidine-3-carboxylic acid, dihydrochloride was prepared in a manner analogous to that set forth in the procedure for compound 10, except (tert-butoxycarbonyl)-L-valine was used as the carboxylic acid in the reaction with 7. The final compound was obtained as a mixture of rotamers, at room temperature. $^1$H-NMR (D$_2$O, 400 MHz): δ$_H$: 4.10 (1H, m), 3.96-3.87 (2H, m), 3.42-3.36 (1H, m), 3.07-2.91 (1H, m), 2.55 (0.7H, m) and 2.40 (0.3H, m), 2.11 (1H, m), 1.51 (1H, m), 1.34-1.10 (3H, m), 0.92 (3H, d, J=6.9 Hz), 0.87 (3H, d, J=6.9 Hz), 0.65 (2H, m). LC-MS: ESI+ (0.1% HCOOH in IPA/water): m/z for $C_{11}H_{26}BN_3O_5$: expected 315.2, observed 326.3 (M+H+HCOOH—H$_2$O)$^+$, 298.3 (M+H–H$_2$O)$^+$, 280.3 (M+H–2H$_2$O)$^+$, ESI–: 296.2 (M–H–H$_2$O)$^-$.

(3R,4S)-3-Amino-1-((S)-2-amino-3-hydroxypropanoyl)-4-(3-boronopropyl)pyrrolidine-3-carboxylic Acid, dihydrochloride (15)

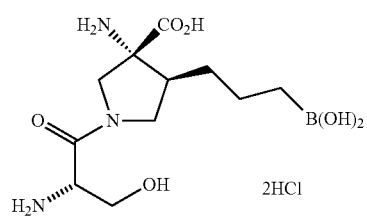

15

(3R,4S)-3-amino-1-((S)-2-amino-3-hydroxypropanoyl)-4-(3-boronopropyl)pyrrolidine-3-carboxylic acid, dihydrochloride was prepared in a manner analogous to that set forth in the procedure for compound 10, except (S)-3-(tert-butoxycarbonyl)-2,2-dimethyloxazolidine-4-carboxylic acid was used as the carboxylic acid in the reaction with 7. The final compound was isolated as a 2:1 mixture of rotamers at room temperature. ¹H-NMR (D₂O, 400 MHz): δ$_H$: 4.21 (1H, m), 4.11 (1H, d, J=13.0 Hz), 3.93 (1H, dd, J=11.5, 8.6 Hz), 3.86-3.74 (2H, m), 3.47 (1H, m), 3.04-2.96 (1H, m), 2.56 (0.7H, m) and 2.44 (0.3H, m), 1.51 (1H, m), 1.29-1.12 (3H, m), 0.64 (2H, m). LC-MS: ESI+ (0.1% HCOOH in IPA/water): m/z for $C_{11}H_{22}BN_3O_6$: expected 303.16, observed 314.2 (M+H+HCOOH−H₂O)⁺, 286.2 (M+H−H₂O)⁺, 268.2 (M+H−2H₂O)⁺, ESI−: 284.1 (M−H−H₂O)⁻.

trans-3-amino-1-((S)-2-amino-3-(1H-imidazol-4-yl)propanoyl)-4-(3-boronopropyl)pyrrolidine-3-carboxylic Acid, trihydrochloride (16)

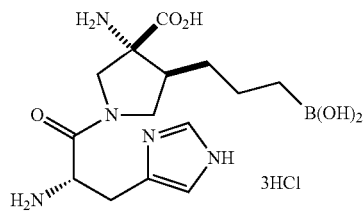

16 trans-3-amino-1-((S)-2-amino-3-(1H-imidazol-4-yl)propanoyl)-4-(3-boronopropyl)pyrrolidine-3-carboxylic acid, trihydrochloride was prepared in a manner analogous to that set forth in the procedure for compound 10, except (tert-butoxycarbonyl)-L-histidine was used as the carboxylic acid, and racemic 5 was used instead of 5a. ¹H-NMR (D₂O, 400 MHz): δ$_H$: 8.57 (1H, d, J=9.0 Hz), 7.33 (1H, d, J=16.9 Hz), 4.20-3.70 (3H, m), 3.51 (1H, m), 3.37-3.24 (3H, m), 2.58 (1H, m), 1.50 (1H, m), 1.39-1.11 (3H, m) and 0.68 (2H, m). LC-MS: ESI+ (0.1% HCOOH in IPA/water): m/z for $C_{14}H_{24}BN_5O_5$: expected 353.18, observed 354.41 (M+H)⁺, 336.44 (M+H−H₂O)⁺, 318.49 (M+H−2H₂O)⁺.

(3R,4S)-3-amino-4-(3-boronopropyl)-1-glycylpyrrolidine-3-carboxylic Acid (17)

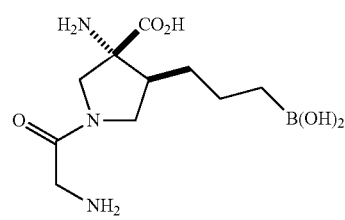

17

(3R,4S)-3-amino-4-(3-boronopropyl)-1-glycylpyrrolidine-3-carboxylic acid was prepared in a manner analogous to that set forth in the procedure for compound 13, except (tert-butoxycarbonyl)glycine was used as the carboxylic acid in the reaction with 7. The final compound was isolated as a 3:2 mixture of rotamers at room temperature. ¹H-NMR (D₂O, 400 MHz): δ$_H$: 4.08-3.83 (2H, m), 3.91 (2H, d, J=4.6 Hz), 3.63-3.53 (1H, m), 3.40-3.22 (1H, m), 2.57-2.37 (1H, m), 1.61 (1H, m), 1.50-1.35 (2H, m), 1.25 (1H, m) and 0.78 (2H, m). LC-MS: ESI+ (0.1% HCOOH in IPA/water): m/z for $C_{10}H_{20}BN_3O_5$: expected 273.15, observed 256.2 (M+H−H₂O)⁺, 238.2 (M+H−2H₂O)⁺; ESI−: 254.2 (M−H−H₂O)⁻.

(3R,4S)-3-amino-1-(2-amino-2-methylpropanoyl)-4-(3-boronopropyl)pyrrolidine-3-carboxylic Acid (18)

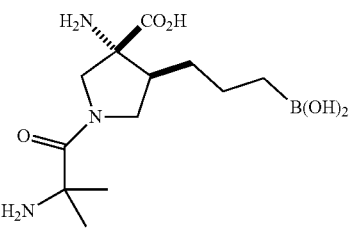

18

(3R,4S)-3-amino-1-(2-amino-2-methylpropanoyl)-4-(3-boronopropyl)pyrrolidine-3-carboxylic acid was prepared in a manner analogous to that set forth in the procedure for compound 13, except 2-((tert-butoxycarbonyl)amino)-2-methylpropanoic acid was used as the carboxylic acid in the reaction with 7. The final compound was isolated as a 2.1 mixture of rotamers at room temperature. ¹H-NMR (D₂O, 400 MHz): O$_H$: 4.38-3.88 (2H, m), 3.72-3.63 (1H, m), 3.40-3.08 (1H, m), 2.75-2.52 (1H, m), 1.71 and 1.69 (4H, s and 2H, s, CMe₂ 2:1 rotamers), 1.64 (1H, m), 1.55-1.41 (2H, m), 1.31 (1H, m) and 0.81 (2H, m). LC-MS: ESI+ (0.1% HCOOH in IPA/water): m/z for $C_{12}H_{24}BN_3O_5$: expected 301.18, observed 284.0 (M+H−H₂O)⁺, 266.0 (M+H−2H₂O)⁺, ESI−: 281.8 (M−H−H₂O)⁻.

(3R,4S)-3-amino-1-((S)-2-aminobutanoyl)-4-(3-boronopropyl)pyrrolidine-3-carboxylic Acid (19)

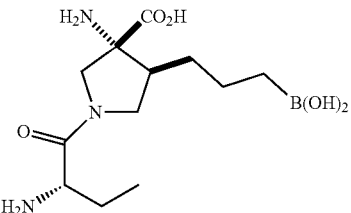

19

(3R,4S)-3-amino-1-((S)-2-aminobutanoyl)-4-(3-boronopropyl)pyrrolidine-3-carboxylic acid was prepared in a manner analogous to that set forth in the procedure for compound 13, except (S)-2-((tert-butoxycarbonyl)amino)butanoic acid was used as the carboxylic acid in the reaction with 7. The final compound was isolated as a 2:1 mixture of rotamers at room temperature. ¹H-NMR (D₂O, 400 MHz): δ$_H$: 4.07-3.87 (3H, m), 3.62-3.27 (2H, m), 2.45-2.17 (1H, m), 1.80 (2H, m), 1.58 (1H, m), 1.50-1.33 (2H, m), 1.21 (1H, m), 0.99 (3H, m) and 0.79 (2H, m). LC-MS: ESI+ (0.1% HCOOH in IPA/water): m/z for $C_{12}H_{24}BN_3O_5$: expected 301.18, observed 284.2 (M+H−H₂O)⁺; ESI−: 282.4 (M−H−H₂O)⁻.

(3R,4S)-3-amino-1-((S)-2-amino-3,3-dimethylbutanoyl)-4-(3-boronopropyl)pyrrolidine-3-carboxylic Acid (20)

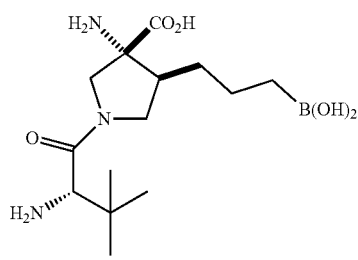

20

(3R,4S)-3-amino-1-((S)-2-amino-3,3-dimethylbutanoyl)-4-(3-boronopropyl)pyrrolidine-3-carboxylic acid was prepared in a manner analogous to that set forth in the procedure for compound 13, except (S)-2-((tert-butoxycarbonyl)amino)-3,3-dimethylbutanoic acid was used as the carboxylic acid in the reaction with 7. The final compound was isolated as a 2:1 mixture of rotamers at room temperature. $^1$H-NMR (D$_2$O, 400 MHz): $\delta_H$ 4.21-3.92 (2H, m), 3.81 [(0.67H, s) and 3.71 (0.33H, s) 2:1 rotamers CHN], 3.66-3.33 (2H, m), 2.47-2.17 (1H, m), 1.59 (1H, m), 1.51-1.35 (2H, m), 1.23 (1H, m), 1.06 and 1.04 [(6H, s) and (3H, s) tBu 2:1 rotamers] and 0.81 (2H, m). LC-MS: ESI+ (0.1% HCOOH in IPA/water): m/z for C$_{14}$H$_{28}$BN$_3$O$_5$: expected 329.21, observed 312.4 (M+H–H$_2$O)$^+$, 294.4 (M+H–2H$_2$O)$^+$, ESI–: 310.4 (M–H–H$_2$O)$^-$.

(3R,4S)-3-amino-1-(1-aminocyclopropane-1-carbonyl)-4-(3-boronopropyl)pyrrolidine-3-carboxylic Acid (21)

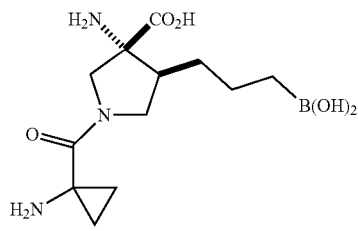

21

(3R,4S)-3-amino-1-(1-aminocyclopropane-1-carbonyl)-4-(3-boronopropyl)pyrrolidine-3-carboxylic acid was prepared in a manner analogous to that set forth in the procedure for compound 13, except (S)-2-((tert-butoxycarbonyl)amino)-2-cyclopropylacetic acid was used as the carboxylic acid in the reaction with 7. The final compound was isolated as a 3:2 mixture of rotamers at room temperature. $^1$H-NMR (D$_2$O, 400 MHz): $\delta_H$: 4.37-3.99 (2H, m), 3.85-3.30 (2H, m), 2.54-2.38 (1H, m), 1.61 (1H, m), 1.47-1.33 (2H, m), 1.24 (1H, m), 1.09 (1H, m) 0.97 (1H, m), 0.89 (2H, m) and 0.81 (2H, m). LC-MS: ESI+ (0.1% HCOOH in IPA/water): m/z for C$_{12}$H$_{22}$BN$_3$O$_5$: expected 299.17, observed 282.1 (M+H–H$_2$O)$^+$, 264.1 (M+H–2H$_2$O)$^+$, ESI–: 280.2 (M–H–H$_2$O)$^-$.

Example 2: Oral Bioavailability Studies

Compound dosing solutions were prepared at 2.5 and 5 mg/mL in water. Female C57BL/6 mice (16-20 g) from Charles River Laboratories (Hollister, Calif.) were housed in cages for at least 3 days prior to dosing. PicoLab 5053 irradiated rodent diet was provided ad libitum throughout the study. Compounds were administered once to the appropriate animals by oral gavage at either 25 or 50 mg/kg (10 mL/kg). Blood samples were collected (3 animals per time point) at 30 min and 1, 2, 4, 8 hr post-dose for the 25 mg/kg studies, and at 1 hour for the 50 mg/kg studies. The blood samples were maintained on wet ice and then centrifuged for 10 min in a refrigerated centrifuge. The resultant plasma was separated, transferred to labeled polypropylene tubes and stored frozen in a freezer set to maintain under –70° C. until analysis.

The plasma samples were analyzed by an LC-MS system. 50 μL of a plasma sample was mixed with 100 μL of acetonitrile/water (80:20) with 0.1% TFA containing 100 ng/mL of an internal standard. The mixture was vortexed and centrifuged. 30 μL of the supernatant was transferred to a 96-well plate containing 90 μL of water with 0.1% formic acid. 20 μL of the resulting solution was injected into a SCIEX QTRAP4000 LC/MS/MS equipped with an electrospray ionization source for quantification.

Oral PK parameters were calculated by noncompartmental analysis of the concentration-time data using Phoenix WinNonLin 6.3 software (Pharsight, Mountain View, Calif.). Area under the concentration-time curve (AUC) was estimated using a linear-up and log-down trapezoidal method, calculated from the dosing time to the last measurable concentration.

AUC for exemplary compounds is shown below:

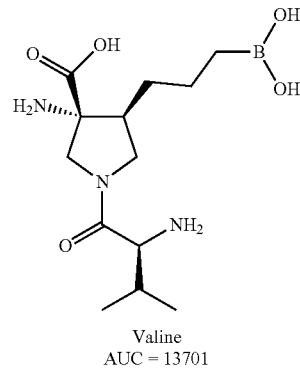

Valine
AUC = 13701

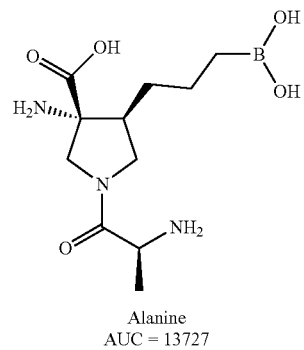

Alanine
AUC = 13727

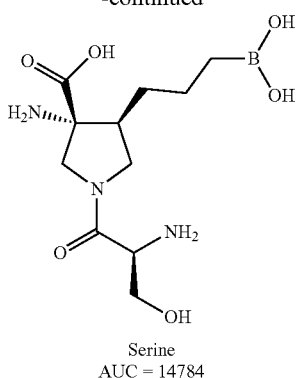

Serine
AUC = 14784

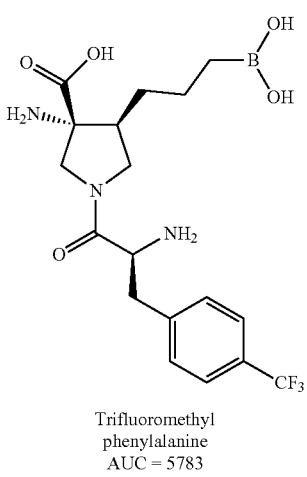

Trifluoromethyl
phenylalanine
AUC = 5783

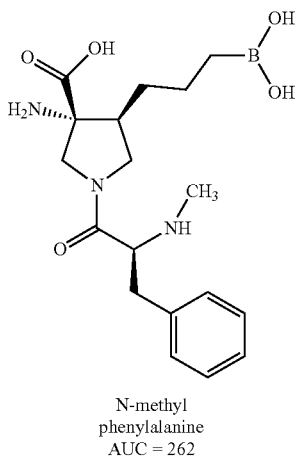

N-methyl
phenylalanine
AUC = 262

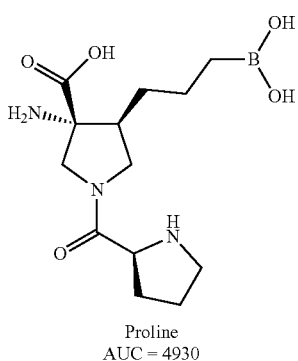

Proline
AUC = 4930

As compared to the proline, trifluoromethyl phenylalanine, and N-methylphenylalanine-derived compounds, the oral exposure for the alanine, valine, and serine derivatives are more favorable.

Example 3: Pharmacokinetic Studies

The pharmacokinetics of the compounds of the invention were studied after administration of a single dose (50 mg/kg) at a single time point (1 hour) in mice. Plasma concentrations were determined as described in Example 2. Results for exemplary compounds are shown below:

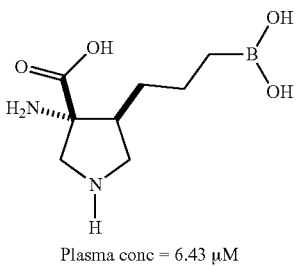

Plasma conc = 6.43 μM

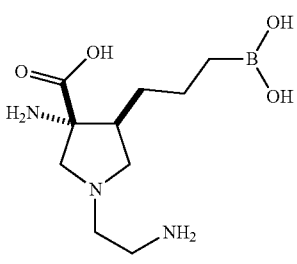

Plasma conc = 1.63 μM

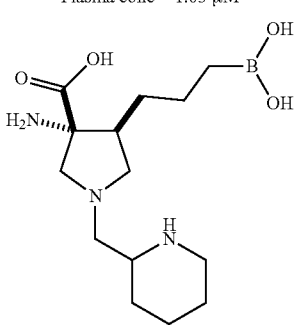

Plasma conc = 0.34 μM

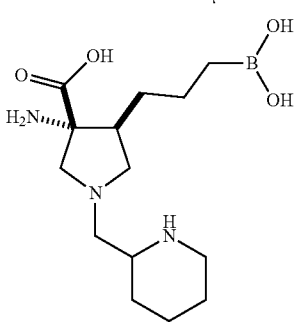

Plasma conc = 4.98 μM

-continued
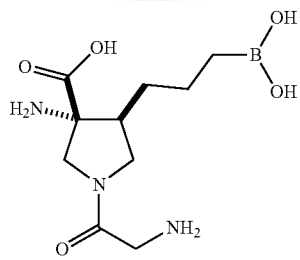
Plasma conc = 18.07 μM
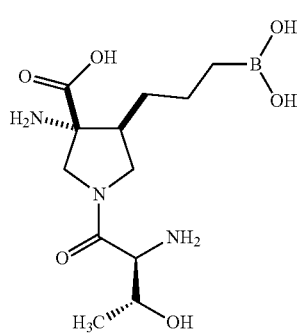
Plasma conc = 26.50 μM
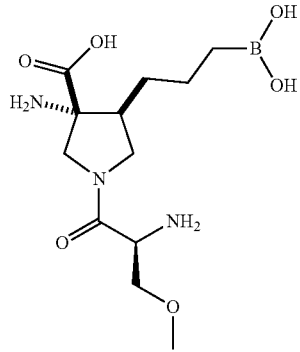
Plasma conc = 53.90 μM
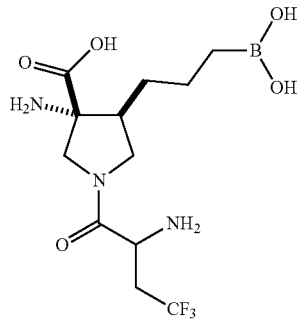
Plasma conc = 32.80 μM
-continued
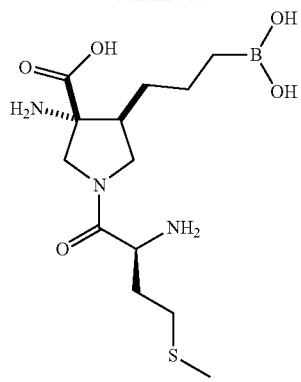
Plasma conc = 31.95
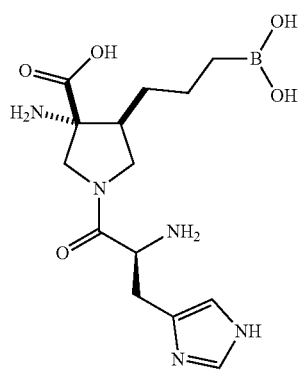
Plasma conc = 28.67 μM
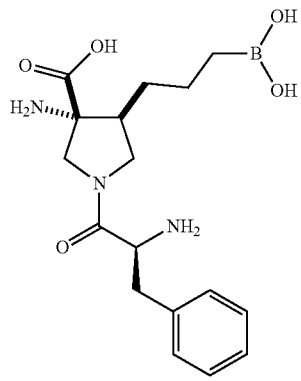
Plasma conc = 32.13 μM
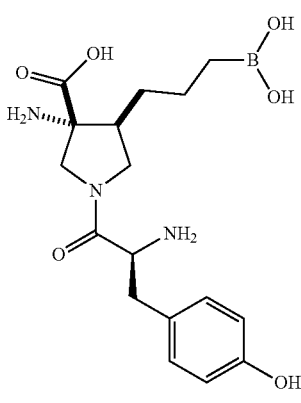
Plasma conc = 22.27 μM -continued
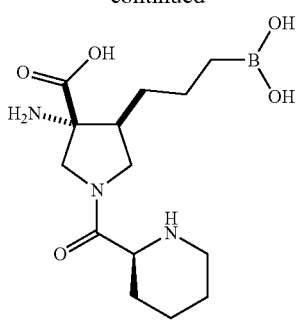
Plasma conc = 22.33 μM
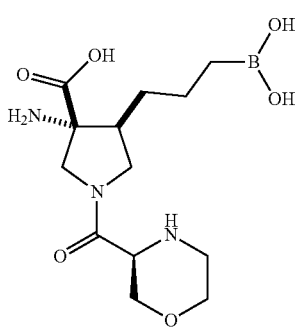
Plasma conc = 8.96 μM
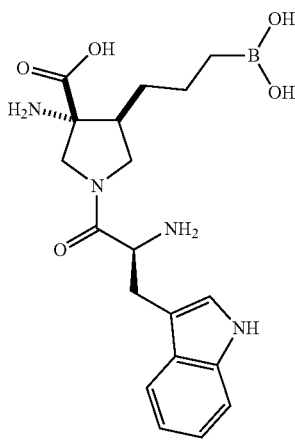
Plasma conc = 30.33 μM
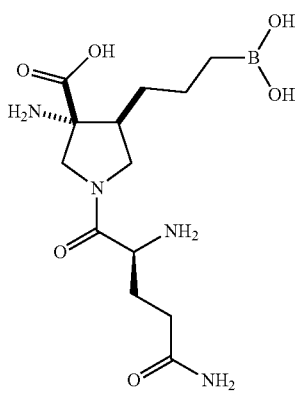
Plasma conc = 14.43 μM
-continued
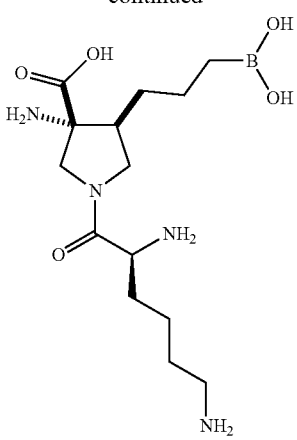
Plasma conc = 30.38 μM
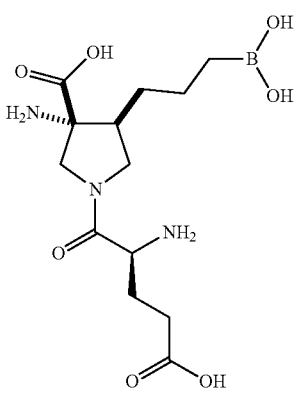
Plasma conc = 10.24 μM
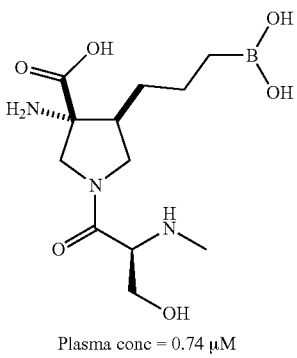
Plasma conc = 0.74 μM
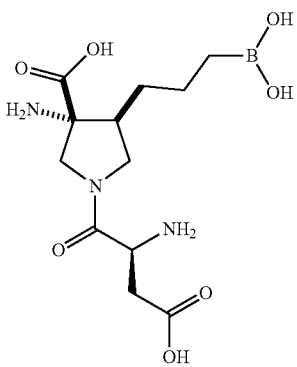
Plasma conc = 8.24 μM -continued

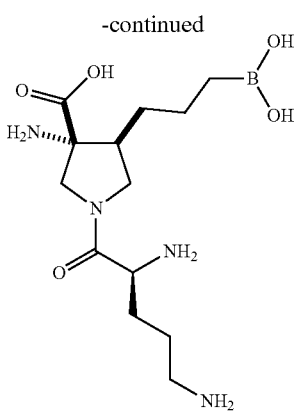

Plasma conc = 14.83 µM

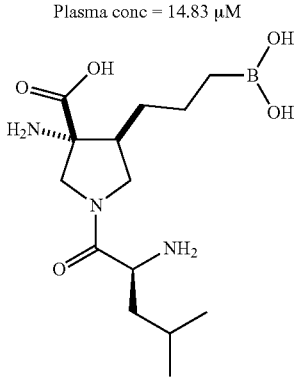

Plasma conc = 65.60 µM

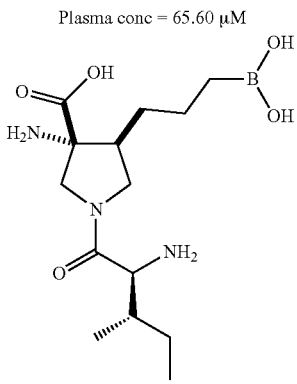

Plasma conc = 41.03 µM

Example 4: Single-Agent Anti-Tumor Activity of Compound 10

Lewis Lung Carcinoma Efficacy Study

Female C57.Bl/6 mice (n=40) were implanted subcutaneously with $1 \times 10^6$ Lewis Lung Carcinoma cells suspended in PBS. The day following implantation, mice were randomized into 4 groups of n=10 mice to receive the following treatments dosed orally twice daily until study end: 1) Vehicle (water); 2) Compound 10 at 50 mg/kg formulated in water; 3) Compound 10 at 100 mg/kg formulated in water; or 4) Compound 10 at 200 mg/kg formulated in water. Tumors were measured three times per week with digital calipers and tumor volumes calculated with the following formula: tumor volume $(mm^3)=(a \times b^2/2)$ where 'b' is the smallest diameter and 'a' is the largest perpendicular diameter. *P-value<0.001, **P-value<0.0001 (Two-sided T-test). Results are shown in FIG. 1.

Madison 109 Efficacy Study

Figure 2:
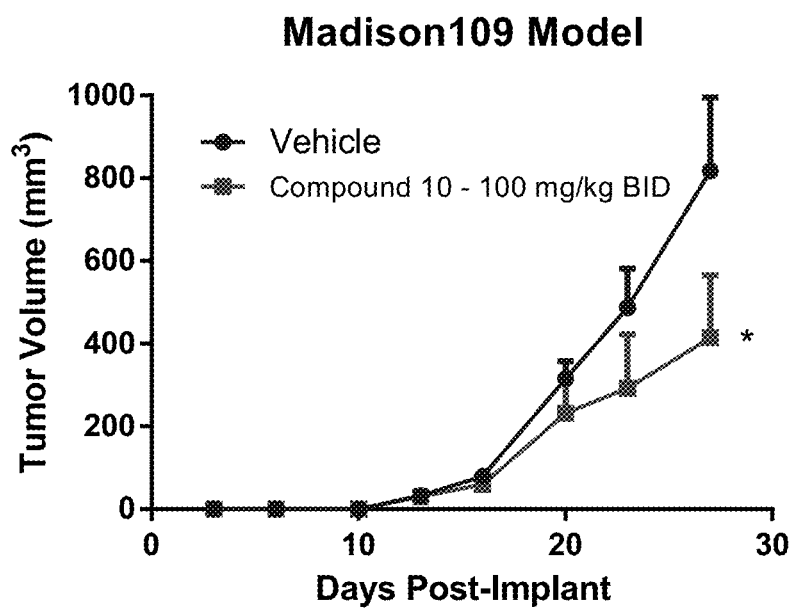
FIG. 2 is a graph depicting the tumor volume over time. Madison 109 murine lung carcinoma cells were implanted in balb/c mice and mice were dosed orally with vehicle or arginase inhibitor Compound 10 BID (N=10 per group).

Female balb/c mice (n=20) were implanted subcutaneously with $5 \times 10^4$ Madison 109 murine lung carcinoma cells suspended in PBS. The day following implantation, mice were randomized into 2 groups of n=10 mice to receive the following treatments dosed orally twice daily until study end: 1) Vehicle (water); or 2) Compound 10 at 100 mg/kg formulated in water. Tumors were measured three times per week with digital calipers and tumor volumes calculated with the following formula: tumor volume $(mm^3)=(a \times b^2/2)$ where 'b' is the smallest diameter and 'a' is the largest perpendicular diameter. *P-value<0.05 (Two-sided T-test). Results are shown in FIG. 2.

B16 Efficacy Study

Figure 3:
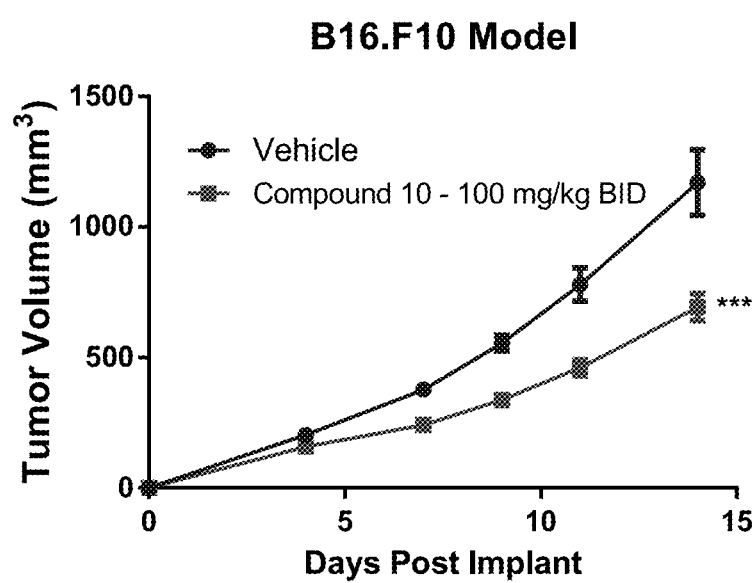
FIG. 3 is a graph depicting the tumor volume over time. B16F10 murine melanoma cells were implanted in C57.Bl/6 mice and mice were dosed orally with vehicle or arginase inhibitor Compound 10 BID (N=10 per group).

Female C57.Bl/6 mice (n=20) were implanted subcutaneously with $2 \times 10^6$ B16F10 murine melanoma cells suspended in PBS. The day following implantation, mice were randomized into 2 groups of n=10 mice to receive the following treatments dosed orally twice daily until study end: 1) Vehicle (water); or 2) Compound 10 at 100 mg/kg formulated in water. Tumors were measured three times per week with digital calipers and tumor volumes calculated with the following formula: tumor volume $(mm^3)=(a \times b^2/2)$ where 'b' is the smallest diameter and 'a' is the largest perpendicular diameter. ***P-value<0.001 (Two-sided T-test). Results are shown in FIG. 3.

Example 5: 4T1 Combination Therapy Studies

Figure 4:
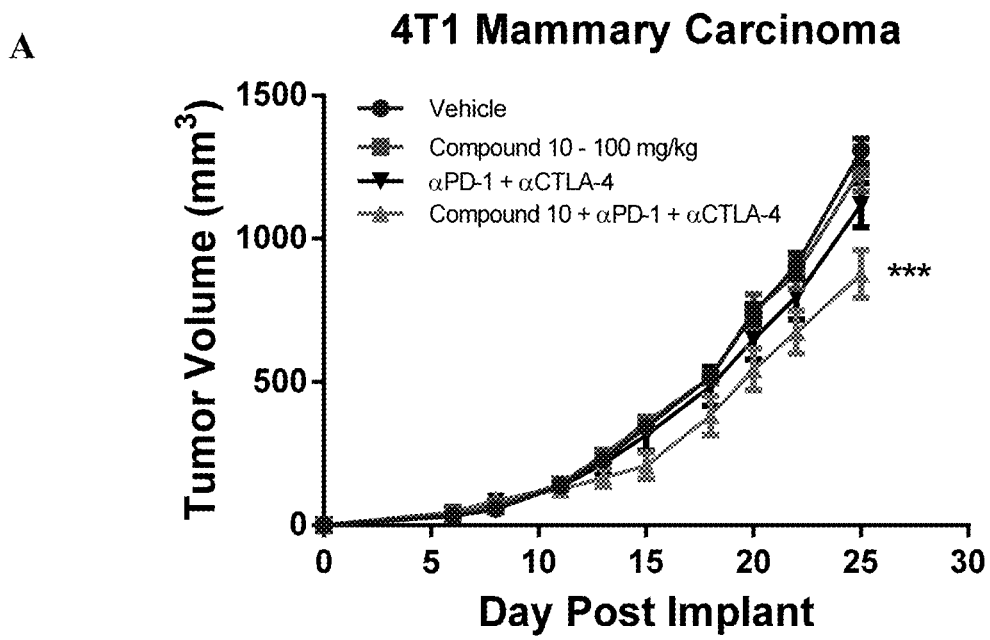
FIG. 4 consists of panels A and B, and depicts the growth of 4T1 mammary carcinoma cells implanted orthotopically into female balb/c mice and treated with either vehicle; Compound 10 (100 mg/kg PO BID); anti-CTLA-4 (5 mg/kg IP on Days 2, 5, 8) plus anti-PD-1 (5 mg/kg IP on days 3, 6, and 9); or the combination of Compound 10 with anti-CTLA-4 and anti-PD-1 (N=10 per group; *P<0.05; *P<0.001, **P<0.0001 vs vehicle).
Figure 4:
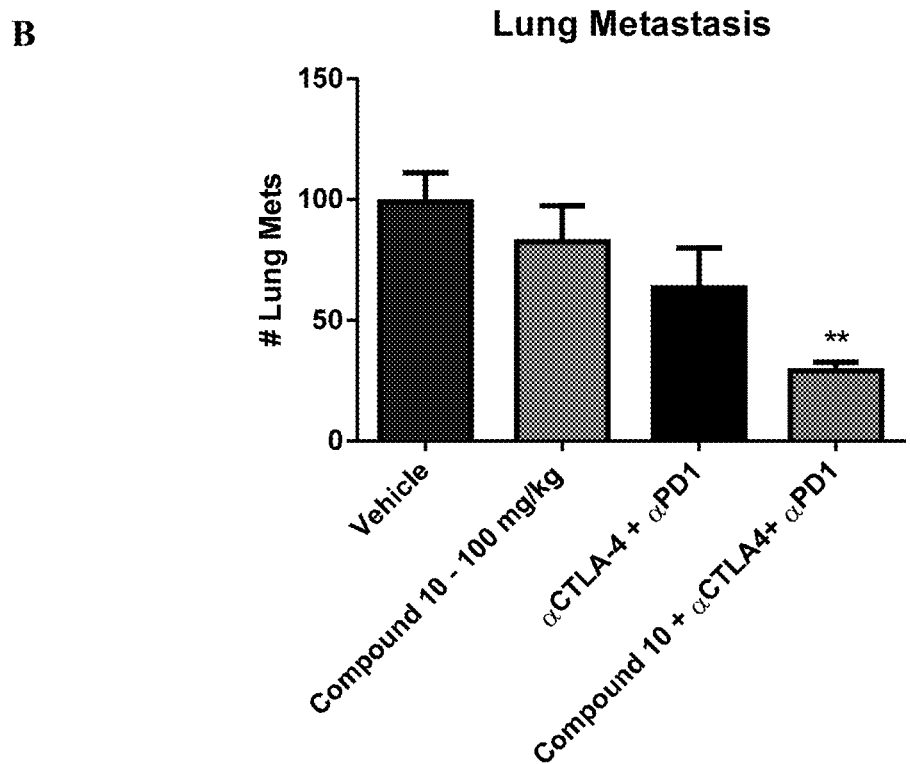
Figure 5:
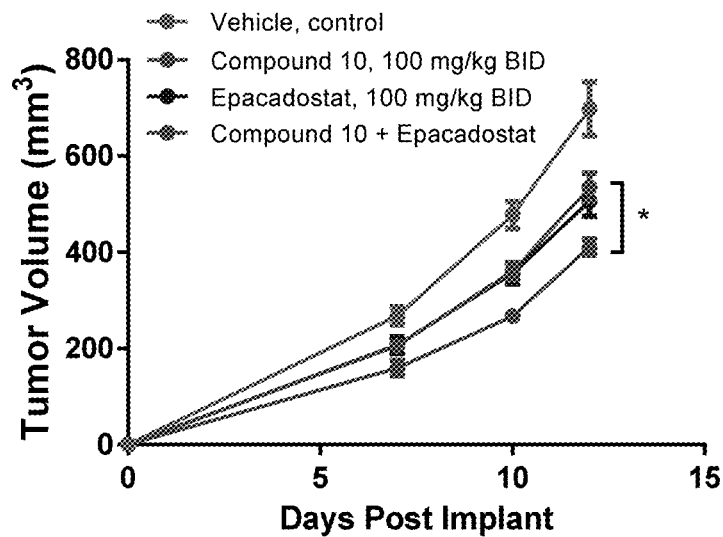
FIG. 5 is a graph depicting the tumor volume over time. Female C57.Bl/6 mice were implanted subcutaneously with $1\times10^6$ B16.F10 murine melanoma cells. On Day 2, mice were randomized into the following groups of n=10 mice; 1) Vehicle PO BID; 2) Compound 10, 100 mg/kg PO BID; 3) Epacadostat, 100 mg/kg PO BID; or 4) Compound 10 and Epacadostat (100 mg/kg PO BID each). Tumors were measured with calipers three times per week and tumor volume calculated using the formula tumor volume $(mm^3)=(a\times b^2/2)$ where 'b' is the smallest diameter and 'a' is the largest perpendicular diameter. *P-value<0.05 (ANOVA).
Figure 6:
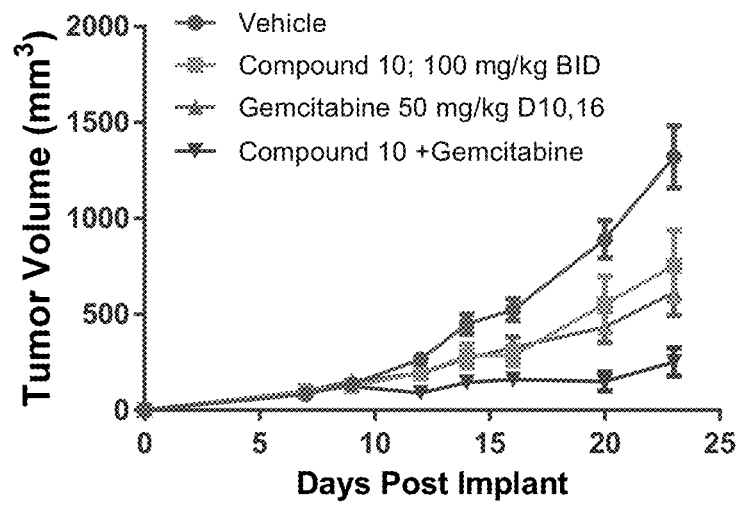
FIG. 6 is a graph depicting the tumor volume over time. Female balb/c mice were implanted subcutaneously with $1\times10^6$ CT26 murine colon carcinoma cells. On Day 2, mice were randomized into the following groups of n=10 mice; 1) Vehicle PO BID starting day 2; 2) Compound 10, 100 mg/kg PO BID starting day 2; 3) Gemcitabine, 50 mg/kg IP on days 10 and 16; or 4) Compound 10 and Gemcitabine at their respective regimens. Tumors were measured with calipers three times per week and tumor volume calculated using the formula tumor volume $(mm^3)=(a\times b^2/2)$ where 'b' is the smallest diameter and 'a' is the largest perpendicular diameter. *P-value<0.05 (ANOVA).
Figure 7:
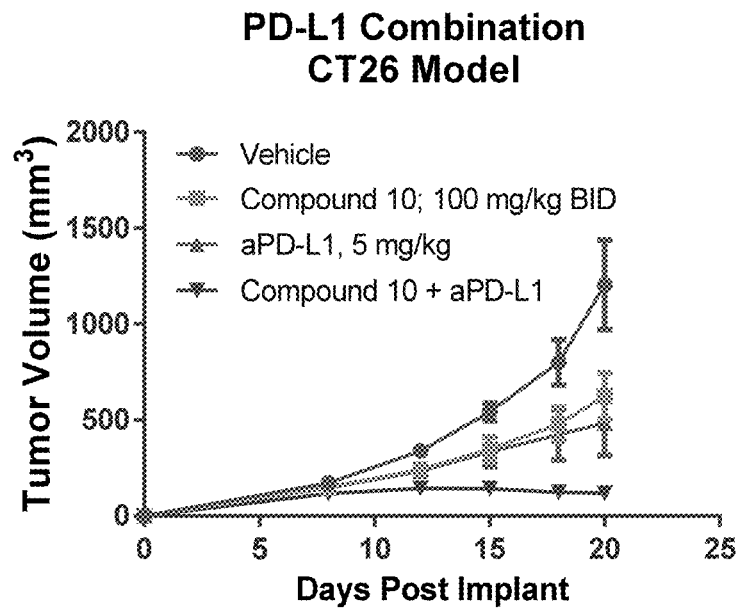
FIG. 7 is a graph depicting the tumor volume over time. Female balb/c mice were implanted subcutaneously with $1\times10^6$ CT26 murine colon carcinoma cells. On Day 2, mice were randomized into the following groups of n=10 mice; 1) Vehicle PO BID; 2) Compound 10, 100 mg/kg PO BID; 3) anti-PD-L1 (clone 10f.9g2), 5 mg/kg IP on days 5, 7, 9, 11, 13, and 15; or 4) Compound 10 and anti-PD-L1. Tumors were measured with calipers three times per week and tumor volume calculated using the formula tumor volume $(mm^3)=(a\times b^2/2)$ where 'b' is the smallest diameter and 'a' is the largest perpendicular diameter.
Figure 8:
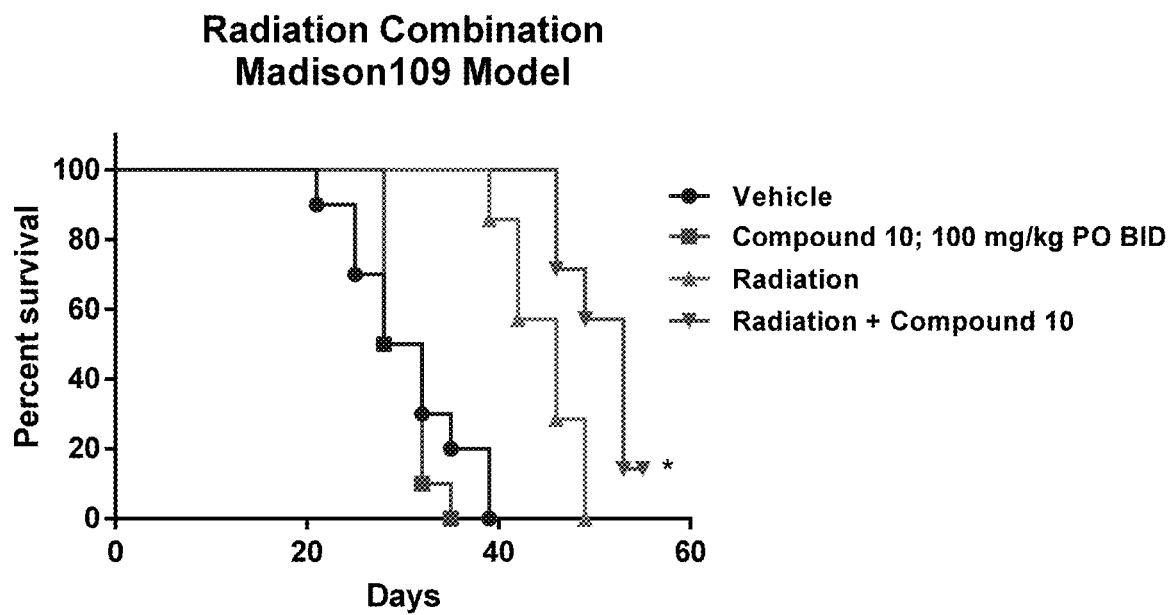
FIG. 8 depicts the percent survival over time. Female balb/c mice were implanted subcutaneously with $5\times10^4$ Madison 109 murine lung carcinoma cells. On Day 2, mice were randomized into the following groups of n=10 mice; 1) Vehicle PO BID; 2) Compound 10, 100 mg/kg PO BID; 3) Whole body radiation (X-ray) 2 gy on Days 10-14 and days 17-21; or 4) Compound 10 and radiation. Tumors were measured with calipers two times per week and tumor volume calculated using the formula tumor volume $(mm^3)=(a\times b^2/2)$ where 'b' is the smallest diameter and 'a' is the largest perpendicular diameter. *P value<0.05 (log-rank test).

Female balb/c mice (n=40) were implanted in the mammary fat pad with $1 \times 10^5$ 4 T1 murine mammary carcinoma cells suspended in PBS. The day following implantation, mice were randomized into 4 groups of n=10 mice each to receive the following treatments: 1) Vehicle (water) dosed orally twice daily until study end; 2) Compound 10 at 100 mg/kg formulated in water dosed orally twice daily until study end; 3) The combination of anti-PD-1 (clone RMPI-14) dosed IP at 5 mg/kg on days 3, 6, and 9 post-implant plus anti-CTLA-4 (clone 9H10) dosed IP at 5 mg/kg on days 2, 5, and 8 post-dose; or 4) the triple combination of compound 10 plus anti-PD-1 plus anti-CTLA-4 at their respective regimens. Tumors were measured three times per week with digital calipers and tumor volumes calculated with the following formula: tumor volume $(mm^3)=(a \times b^2/2)$ where 'b' is the smallest diameter and 'a' is the largest perpendicular diameter. ***P-value<0.001 (Two-sided T-test). On day 25, mice were sacrificed and lungs perfused with India Ink (25% in PBS) then harvested and fixed in 100% ethanol: 10% neutral buffered formalin: acetic acid mixture at 10:1: 0.5 ratio. The number of lung metastases was counted manually in a blinded manner. Results are shown in FIG. 4.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of treating cancer, comprising administering to a subject in need thereof a therapeutically effective amount of a compound of the formula

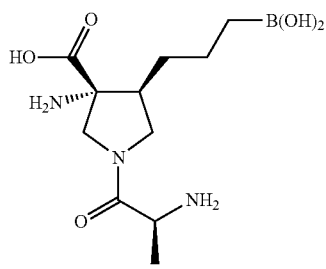 [SMILES: C[C@H](N)C(=O)N1C[C@H](CCCB(O)O)[C@](N)(C(=O)O)C1]

or a pharmaceutically acceptable salt thereof.

2. The method of claim 1, wherein the cancer is selected from acute myeloid leukemia (AML), bladder cancer, breast cancer, colorectal cancer, chronic myelogenous leukemia (CML), esophageal cancer, gastric cancer, lung cancer, melanoma, mesothelioma, non-small cell lung carcinoma (NSCLC), ovarian cancer, pancreatic cancer, prostate cancer, renal cancer, skin cancer, bile duct cancer, multiple myeloma, adrenocortical carcinoma, head and neck cancer, and endometrial cancer.

3. The method of claim 1 comprising conjointly administering one or more additional chemotherapeutic agents.

4. The method of claim 3, wherein the one or more additional chemotherapeutic agents includes aminoglutethimide, amsacrine, anastrozole, asparaginase, AZD5363, Bacillus CalmetteGurin vaccine (bcg), bicalutamide, bleomycin, bortezomib, buserelin, busulfan, campothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, erlotinib, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, nilutamide, nocodazole, octreotide, olaparib, oxaliplatin, paclitaxel, pamidronate, pazopanib, pentostatin, perifosine, plicamycin, pomalidomide, porfimer, procarbazine, raltitrexed, rituximab, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, or vinorelbine.

5. The method of claim 3, wherein the one or more additional chemotherapeutic agents includes abagovomab, adecatumumab, afutuzumab, alemtuzumab, anatumomab mafenatox, apolizumab, atezolizumab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, ocaratuzumab, ofatumumab, olatatumab, pembrolizumab, pidilizumab, rituximab, ticilimumab, samalizumab, or tremelimumab.

6. The method of claim 3, wherein the one or more additional chemotherapeutic agents includes abagovomab, adecatumumab, afutuzumab, anatumomab mafenatox, apolizumab, blinatumomab, catumaxomab, durvalumab, epratuzumab, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab.

7. The method of claim 6, wherein the one or more additional chemotherapeutic agents includes ipilimumab, nivolumab, pembrolizumab, or pidilizumab.

8. The method of claim 1, wherein the method further comprises administering one or more non-chemical methods of cancer treatment selected from, such as radiation therapy, surgery, thermoablation, focused ultrasound therapy, cryotherapy, or a combination of the foregoing.

9. The method of claim 1, wherein the cancer is selected from bladder cancer, colorectal cancer, esophageal cancer, gastric cancer, lung cancer, melanoma, mesothelioma, non-small cell lung carcinoma (NSCLC), ovarian cancer, renal cancer, bile duct cancer, multiple myeloma, adrenocortical carcinoma, head and neck cancer, and endometrial cancer.

10. The method of claim 1, wherein the cancer is bladder cancer.

11. The method of claim 1, wherein the cancer is colorectal cancer.

12. The method of claim 1, wherein the cancer is esophageal cancer.

13. The method of claim 1, wherein the cancer is gastric cancer.

14. The method of claim 1, wherein the cancer is lung cancer.

15. The method of claim 1, wherein the cancer is melanoma.

16. The method of claim 1, wherein the cancer is mesothelioma.

17. The method of claim 1, wherein the cancer is pancreatic cancer.

18. The method of claim 1, wherein the cancer is non-small cell lung carcinoma (NSCLC).

19. The method of claim 1, wherein the cancer is ovarian cancer.

20. The method of claim 1, wherein the cancer is renal cancer.

21. The method of claim 1, wherein the cancer is bile duct cancer.

22. The method of claim 1, wherein the cancer is multiple myeloma.

23. The method of claim 1, wherein the cancer is adrenocortical carcinoma.

24. The method of claim, 1, wherein the cancer is head and neck cancer.

25. The method of claim 1, wherein the cancer is endometrial cancer.

26. A method of treating cancer, comprising administering to a subject in need thereof a therapeutically effective amount of a boronic acid ester derivative of the compound of the formula

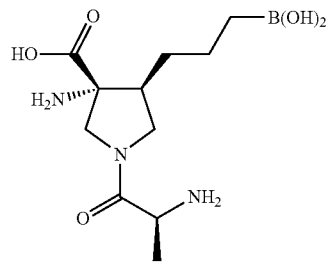 [SMILES: C[C@H](N)C(=O)N1C[C@H](CCCB(O)O)[C@](N)(C(=O)O)C1]

or a pharmaceutically acceptable salt thereof, wherein the boronic acid moiety of the compound is esterified to form a boronic acid ester derivative.

27. The method of claim 26, wherein the boronic acid ester derivative is capable of hydrolyzing under physiologic conditions to form the compound of the formula

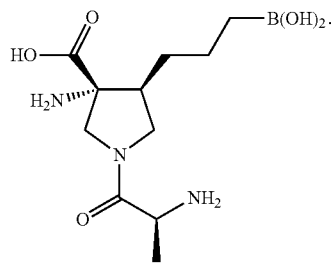 [SMILES: C[C@H](N)C(=O)N1C[C@H](CCCB(O)O)[C@](N)(C(=O)O)C1]

28. The method of claim 26, wherein the boronic acid ester derivative is a citrate or tartrate ester.

29. The method of claim 26, wherein the cancer is selected from bladder cancer, colorectal cancer, esophageal cancer, gastric cancer, lung cancer, melanoma, mesothelioma, non-small cell lung carcinoma (NSCLC), ovarian cancer, renal cancer, bile duct cancer, multiple myeloma, adrenocortical carcinoma, head and neck cancer, and endometrial cancer.

30. A method of treating cancer, comprising administering to a subject in need thereof a therapeutically effective amount of a carboxylic acid ester derivative of the compound of the formula

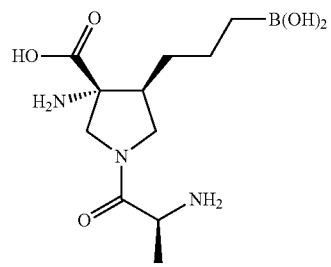 [SMILES: C[C@H](N)C(=O)N1C[C@H](CCCB(O)O)[C@](N)(C(=O)O)C1]

or a pharmaceutically acceptable salt thereof, wherein the carboxylic acid ester on the pyrrolidine ring is esterified to form a carboxylic acid ester.

31. The method of claim 30, wherein the carboxylic acid ester derivative is capable of hydrolyzing under physiologic conditions to form the compound of the formula

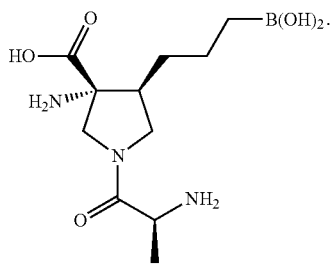 [SMILES: C[C@H](N)C(=O)N1C[C@H](CCCB(O)O)[C@](N)(C(=O)O)C1]

32. The method of claim 30, wherein the cancer is selected from bladder cancer, colorectal cancer, esophageal cancer, gastric cancer, lung cancer, melanoma, mesothelioma, non-small cell lung carcinoma (NSCLC), ovarian cancer, renal cancer, bile duct cancer, multiple myeloma, adrenocortical carcinoma, head and neck cancer, and endometrial cancer.

33. The method of claim 1, wherein the compound, or pharmaceutically acceptable salt thereof, is present as a solvate.

34. The method of claim 33, wherein the solvate is a water solvate, methanol solvate, ethanol solvate or dimethylformamide solvate.

35. The method of claim 26, wherein the compound, or pharmaceutically acceptable salt thereof, is present as a solvate.

36. The method of claim 35, wherein the solvate is a water solvate, methanol solvate, ethanol solvate or dimethylformamide solvate.

37. The method of claim 30, wherein the compound, or pharmaceutically acceptable salt thereof, is present as a solvate.

38. The method of claim 37, wherein the solvate is a water solvate, methanol solvate, ethanol solvate or dimethylformamide solvate.

* * * * *